(12) United States Patent
Port

(10) Patent No.: US 8,268,810 B2
(45) Date of Patent: *Sep. 18, 2012

(54) LIPOPHILIC CHELATES AND THEIR USE IN IMAGING

(75) Inventor: Marc Port, Deuil la Barre (FR)

(73) Assignee: Guerbet, Villepinte (FR)

( * ) Notice: Subject to any disclaimer, the term of this patent is extended or adjusted under 35 U.S.C. 154(b) by 774 days.

This patent is subject to a terminal disclaimer.

(21) Appl. No.: 11/886,911

(22) PCT Filed: Mar. 24, 2006

(86) PCT No.: PCT/EP2006/061034
§ 371 (c)(1),
(2), (4) Date: Jan. 21, 2009

(87) PCT Pub. No.: WO2006/100305
PCT Pub. Date: Sep. 28, 2006

(65) Prior Publication Data
US 2009/0214441 A1    Aug. 27, 2009

(30) Foreign Application Priority Data
Mar. 24, 2005 (FR) ..................... 05 02921

(51) Int. Cl.
A61K 31/555 (2006.01)
C07F 5/00 (2006.01)

(52) U.S. Cl. .......... 514/185; 534/16

(58) Field of Classification Search .......... 424/1.11, 424/1.65, 9.1, 9.3, 9.31, 9.32, 9.362, 9.4
See application file for complete search history.

(56) References Cited

U.S. PATENT DOCUMENTS

| | | | |
|---|---|---|---|
| 5,460,799 A | 10/1995 | Elgavish et al. | |
| 5,614,170 A | 3/1997 | Cacheris et al. | |
| 5,804,164 A | 9/1998 | Elgavish | |
| 5,833,948 A | 11/1998 | Tournier et al. | |
| 5,958,371 A | 9/1999 | Lanza et al. | |
| 6,010,682 A | 1/2000 | Unger et al. | |
| 6,132,764 A | 10/2000 | Li et al. | |
| 6,440,956 B1 | 8/2002 | Port | |
| 6,517,814 B2 | 2/2003 | Liu | |
| 6,719,958 B1 | 4/2004 | Gozzini et al. | |
| 2002/0090342 A1 | 7/2002 | Liu | |
| 2003/0171561 A1 | 9/2003 | Pillai et al. | |
| 2004/0248856 A1 | 12/2004 | Lanza et al. | |

FOREIGN PATENT DOCUMENTS

| | | |
|---|---|---|
| EP | 0 579 802 B1 | 1/1994 |
| WO | WO 91/14178 A1 | 9/1991 |
| WO | WO 92/21017 A1 | 11/1992 |
| WO | WO-94/26315 A1 | 11/1994 |
| WO | WO-00/75141 A1 | 12/2000 |
| WO | WO 02/060524 A3 | 8/2002 |
| WO | WO 03/008390 A1 | 1/2003 |
| WO | WO 03/062198 A1 | 7/2003 |
| WO | WO-03/074523 A2 | 9/2003 |
| WO | WO 2004/087656 A1 | 10/2004 |
| WO | WO-2004/112839 | * 12/2004 |
| WO | WO-2004/112839 A1 | 12/2004 |

OTHER PUBLICATIONS

Vladimir S. Trubetskot, Advanced Drug Delivery Reviews, 37, 81-88, 1999.*
Aime et al., "Designing novel contrast agents for magnetic resonance imaging. Synthesis and relaxometric characterization of three gladolinium(III) complexes based on functionalized pyridine-containing macrocyclic ligands," Helvetica Chimica Acta, vol. 86, No. 3, 2003, pp. 615-532, ISSN: 0018-019X, XP002355606.
Dioury et al., "Synthesis of a new tricyclic tetraazatriacetic acid as ligand for gadolinium(III)," Tetrahedron Letters, vol. 46, No. 4, 2005, pp. 611-613, ISSN: 0040-4039, XP004695928.
Flacke et al., Circulation, 2001, No. 104, pp. 1280-1285.
Hovland et al., J. Chem. Soc., Perkin Trans., 2001, vol. 2, pp. 929-933.

* cited by examiner

Primary Examiner — Michael G Hartley
Assistant Examiner — Jagadishwar Samala
(74) Attorney, Agent, or Firm — Birch, Stewart, Kolasch & Birch, LLP

(57) ABSTRACT

The invention relates to chelate compounds which can be used in MRI, the chelates being intended to be conveyed by lipophilic transporters, such as lipid nanoparticles or liposomes. The invention also relates to compounds comprising, in association, these chelates and these transporters, if appropriate connected via chemical bonding groups, and to their use in diagnostic imaging, it being possible for this association additionally to comprise biological targeting markers, denoted biovectors.

11 Claims, No Drawings

LIPOPHILIC CHELATES AND THEIR USE IN IMAGING

The invention relates to chelate compounds which can be used in MRI, the chelates being intended to be conveyed by lipophilic transporters, such as lipid nanoparticles or liposomes. The invention also relates to compounds comprising, in association, these chelates and these transporters, if appropriate connected via chemical bonding groups, and to their use in diagnostic imaging, it being possible for this association additionally to comprise biological targeting markers, denoted biovectors.

Numerous chelates used in MRI are already known, such as paramagnetic metal ion chelates, in particular DTPA, DOTA or DOTA-bisamide, and also lipophilic derivatives of these compounds described in the documents U.S. Pat. Nos. 5,804,164, 5,460,799 and WO91/14178. Such derivatives are described at the surface of liposomes or in the form of emulsified particles, for example in the documents U.S. Pat. No. 6,132,764, U.S. Pat. No. 6,010,682, U.S. Pat. No. 5,614,170 and U.S. Pat. No. 5,833,948. Such lipid compositions and emulsions comprise, in some cases, molecules denoted as biovectors intended for the specific recognition of regions of diagnostic or therapeutic interest, in particular pathological regions having a modified expression of the target molecules of these biovectors in comparison with normal cells. Emulsions of fluorocarbon nanoparticles comprising biovectors are described for example, in WO 02/060524 and WO 03/062198.

Numerous chelates, for example restated in the document US 2004/0248856, are described or only mentioned in these compositions formed of liposomes or emulsions, in particular the chelates: DTPA, EDTA, DOTA, DTPA-BOA (bisamide), DOTA-PE, DTPA-PE (monoamide), ODDA, TTTA, DOTMA, DOTRP, DO3A or BOPTA.

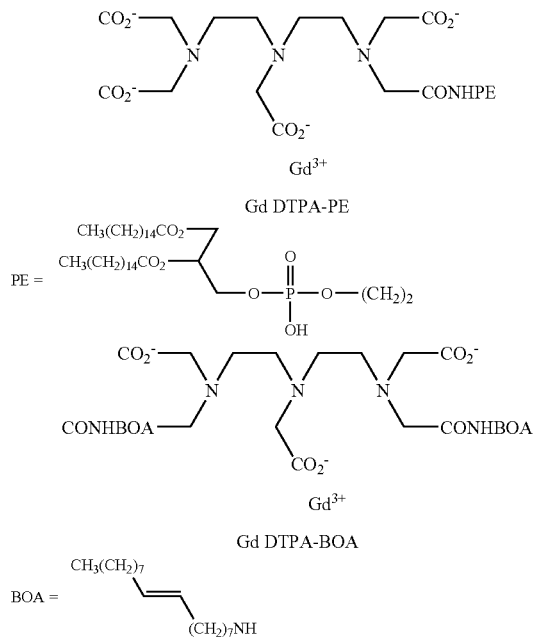

The technology of micro/nanoemulsions has made it possible to prove the concept of specific Ti imaging at picomolar concentrations (150 pM) of nanoparticles (A. M. Morawski, P. M. Winter, S. D. Caruthers et al., Detection of angiogenic epitopes at picomolar concentrations with $\alpha_v\beta_3$-integrin targeted ultra paramagnetic nanoparticles in human cancer cells in vitro. Proc. Intl. Soc. Mag. Reson. Med., 2003, 11, 831):

- in $\alpha_v\beta_3$ targeting: tumor angiogenesis using DM 101 antibodies or a quinolone antagonist (WO 03/062198A) (rabbit cornea models, VX-2, melanoma C32, vasa vasorum of the atheromatous plaque (model New Zealand rabbit on a cholesterol-rich diet).
- in targeting of the tissue factor (TF) using an anti-TF polyclonal antibody in order to treat restenosis (incorporation of doxorubicin in the microemulsion).
- in targeting the thrombus using a biotinylated antifibrin monoclonal antibody (S. Flacke, S. Fischer, M. J. Scott et al., Novel MRI contrast agent for molecular imaging of fibrin: implications for detecting vulnerable plaques. Circulation, 2001, 104, 1280-1285).

Furthermore, derivatives of PCTA type, of formula

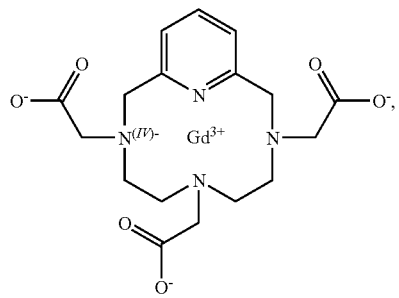

are known (WO 9426315 and U.S. Pat. No. 6,440,956) but which, to the knowledge of the Applicant, exhibit short chains or hydrophilic and nonlipophilic long chains. The chemical structures described do not allow these PCTA derivatives to be used in lipid compositions, in particular of emulsion, liposome, micelle or analogous type. According to a first aspect, the invention relates to novel compounds of the type of chelates of PCTA type not described by the Applicant in the prior art for use in lipid compositions.

The invention relates more specifically to lipophilic chelates of formula (I)

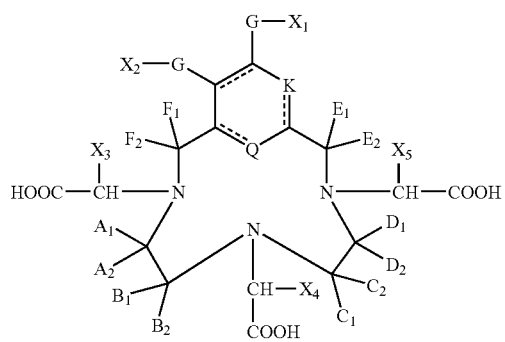

in which:
1) ═represents a single or double bond;
2) Q represents a nitrogen atom or an NH radical;
3) $X_1$, $X_2$, $X_3$, $X_4$ and $X_5$, which are identical or different, independently represent, provided that $X_1$, $X_2$, $X_3$, $X_4$ and $X_5$ are not all H and that at least one of $X_1$, $X_2$, $X_3$, $X_4$ and $X_5$ is a lipophilic group:

3.1) a hydrogen atom;
3.2) a —(CH$_2$)$_a$—CONR$_1$R$_2$, —(CH$_2$)$_a$—NR$_1$COR$_2$ or

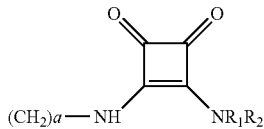

group, with:
  a=1, 2 or 3;
  each R$_1$ or R$_2$ group independently represents an H atom; a substituted or unsubstituted and linear, branched or cyclic C$_7$-C$_{30}$ alkyl or alkenyl chain optionally interrupted by O, NH, NR$_3$ or S, where R$_3$ is a C$_1$-C$_3$ alkyl; or a group

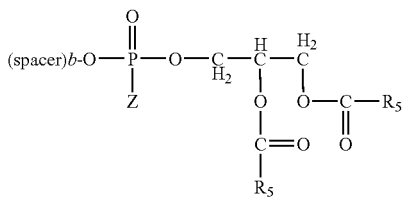

with b=0, 1 or 2, Z represents O$^-$ or OH, R$_5$ represents a saturated or unsaturated and optionally substituted group of at least 6 carbon atoms, advantageously a C$_6$ to C$_{30}$ group, and spacer represents a CH$_2$CH$_2$ or polyalkylene glycol group;
3.3) a group

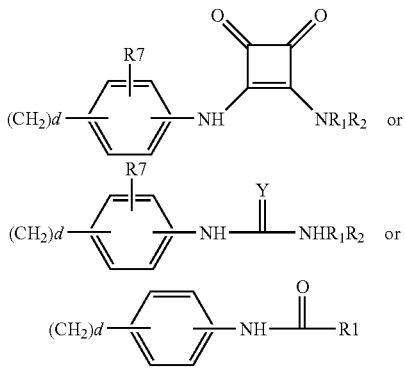

with:
  d between 0 and 3;
  Y chosen from O and S;
  R$_7$ chosen from H, OH, CH$_3$ or OCH$_3$;
  R$_1$ and R$_2$ are as defined above;
4) A$_1$, A$_2$, B$_1$, B$_2$, C$_1$, C$_2$, D$_1$, D$_2$, E$_1$, E$_2$, F$_1$ and F$_2$ represent, independently of one another, an H or CH$_3$ or cyclohexyl group;
5) K represents C or N or CH or NH or N$^+$R$_4$ with R$_4$ a C$_1$-C$_6$ group chosen from alkyl, benzyl or substituted benzyl;
6) G is not present or represents O or NHR$_4$, with R$_4$ as defined above;
and their pharmaceutically acceptable salts.

In particular, the invention relates to a compound of formula (I)

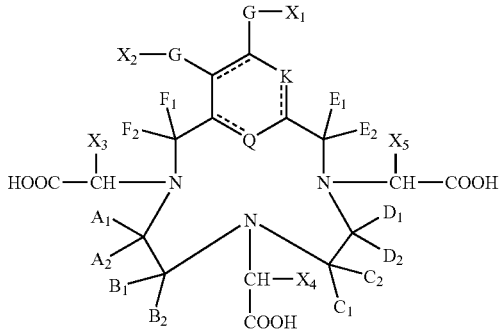

in which:
1) ═represents a single or double bond
2) Q represents a nitrogen atom or an NH radical;
3) X$_1$ or X$_2$, which are identical or different, independently represent a hydrogen atom, a —(CH$_2$)$_a$—CONR$_1$R$_2$, (CH$_2$)$_a$—NR$_1$—COR$_2$ or

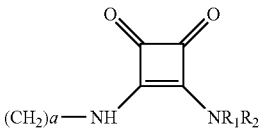

group, with:
  a=1, 2 or 3;
  each R$_1$ or R$_2$ group independently represents an H atom, a substituted or unsubstituted and linear, branched or cyclic C$_7$-C$_{30}$ alkyl or alkenyl chain, or a group

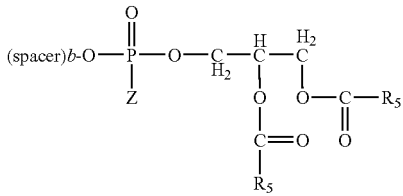

with b=0, 1 or 2, Z represents O$^-$ or OH, R$_5$ represents a saturated or unsaturated and optionally substituted group of at least 6 carbon atoms, advantageously a C$_6$ to C$_{30}$ group, advantageously an alkyl group, and spacer represents a CH$_2$CH$_2$ or polyalkylene glycol group;
4) X$_3$, X$_4$ and X$_5$, which are identical or different, have the same meaning as X$_1$ or X$_2$ provided that X$_1$, X$_2$, X$_3$, X$_4$ and X$_5$ are not all H and at least one of X$_1$, X$_2$, X$_3$, X$_4$ and X$_5$ is a lipophilic group or X$_3$, X$_4$ and X$_5$, which are identical or different, represent

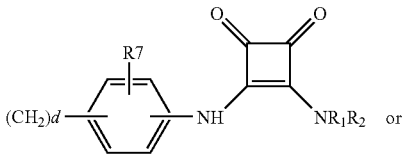

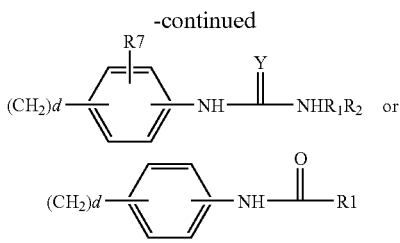

with:
d between 0 and 3;
Y chosen from O and S;
$R_7$ chosen from H, OH, $CH_3$ or $OCH_3$;
$R_1$ and $R_2$ are as defined above;

5) $A_1$, $A_2$, $B_1$, $B_2$, $C_1$, $C_2$, $D_1$, $D_2$, $E_1$, $E_2$, $F_1$ and $F_2$ represent, independently of one another, an H or $CH_3$ or cyclohexyl group;
6) K represents C or N or CH or NH or $N^+R_4$ with $R_4$ a $C_1$-$C_6$ group chosen from alkyl, benzyl or substituted benzyl;
7) G is not present or represents O or $NHR_4$, with $R_4$ as defined above;

and its pharmaceutically acceptable salts.

The expression "at least one of $X_1$, $X_2$, $X_3$, $X_4$ and $X_5$ is a lipophilic group" is understood to mean that these groups $X_1$ to $X_5$ have a lipophilic nature such that they allow the compound (I) to be lipophilic.

More specifically, the groups $X_1$ to $X_5$ are such that the compound (I) exhibits a sufficient lipophilicity to be coupled to a lipophilic transporter, such as a liposome, a micelle or a nanoemulsion. It is specified that the PCTA nucleus of the compound (I) is hydrophilic in the absence of chain $X_1$ to $X_5$.

For example, without implied limitation, a choice of the $X_1$ to $X_5$ groups will be available such that the HLB (hydrophilic/lipophilic balance) value of the chelate (I) is of the order of 13 to 20 for chelates associated with direct micelles or with lipid nanoemulsions, of the order of 1 to 6 for chelates associated with reverse micelles and of the order of 6 to 8 for chelates associated with liposomes. Thus, advantageously, the HLB value of the chelate (I) is between 1 and 20. Advantageously, only one or two of the groups $X_1$ to $X_5$ will be lipophilic, the other groups being short and nonhydrophilic chains, such as represented in Examples 6 and 20 in particular.

Within the meaning of the present invention, the term "$C_7$-$C_{30}$ alkenyl group" is understood to mean any unsaturated, linear or branched, monovalent hydrocarbon radical comprising a double bond and having from 7 to 30 carbon atoms inclusive, unless otherwise indicated.

According to an advantageous implementation, $R_1$ and/or $R_2$ represent a $C_7$-$C_{24}$, preferably $C_8$-$C_{18}$, alkyl or alkenyl chain which is linear or cyclic (for example comprising a phenylene or steroid group). Preferably, $R_1$ and/or $R_2$ represent a linear $C_8$-$C_{18}$ alkyl or alkenyl chain. For example, mention may be made, as examples of lipophilic $X_1$ to $X_5$ chains, of chains of the palmityl, oleyl, linoleyl, lauryl, stearyl, caproyl, capryl, caprylyl, arachidyl and analogous type.

In the case where $X_1$ to $X_5$ represent a $C_7$-$C_{30}$ alkyl or alkenyl chain interrupted by O, NH or $NR_3$, the $X_1$ to $X_5$ groups are such that the chelate of formula (I) is lipophilic. Advantageously, in this case, the $C_7$-$C_{30}$ alkyl or alkenyl chains do not comprise more than two O, NH or $NR_3$ atoms or groups. Any compound equivalent in terms of biological activity in particular to the lipophilic compounds exemplified is, however, within the scope of the invention.

The present invention additionally relates to a complex of a paramagnetic metal ion and of an organic chelate of formula (I) according to the present invention.

It also relates to a complex according to the present invention in which the metal ion is a lanthanide of atomic number 58-70 or a transition metal of atomic number 21-29, 42 or 44.

Moreover, it relates to a complex according to the present invention in which the metal ion is chosen from Gd(III), Mn(II), iron and dysprosium.

These lipophilic chelates and metal complexes are intended to be associated with various types of lipophilic transporters, the product formed by the association between transporter and the chelate or the complex making it possible to generate a signal in medical diagnostic imaging. Advantageously, the MRI relativity of these chelates is better than that obtained with a DOTA or DTPA nucleus.

It is also possible to have K represented by C—$CH_2$—O—R (with R chosen from H, $C_1$-$C_5$ alkyl, benzyl or substituted benzyl) or by C—COO—($C_1$-$C_3$ alkyl), the preparation of such chelates being described in the document EP 579 802, provided that these groups do not detrimentally affect the lipophilicity of the chelate (I). More broadly, it is also possible to have $X_1$ to $X_5$ groups which are written (spacer)-Z, with:

spacer being a bonding group between, on the one hand, —CH— and a lipophilic group other than those exemplified in the present patent application, the spacer comprising a group capable of reacting with a functional group of the lipophilic group (a very large number of spacers can be used, provided that they do not modify in a harmful way the lipophilicity of the chelate), Z being any lipophilic group other than those exemplified in detail in the present patent application.

According to another aspect, the invention thus relates to a compound comprising a chelate of formula (I) or a complex (chelate coupled to a metal) according to the present invention coupled chemically with an appropriate lipophilic transporter preferably chosen from liposomes, fluorocarbon nanoparticles, oil emulsions or micelles. The invention also relates to the diagnostic compositions, in particular the contrast agents, comprising these compounds or complexes or compositions. These chelates are capable of typically chelating paramagnetic metal ions for MRI or radionuclides for scintigraphy and PET (positron emission tomography). The signal makes possible the measurement of a quantified parameter in particular in MRI (relativity) or in scintigraphy or in PET.

The expression compound comprising a chelate of formula (I) includes the case of the use of different chelates of formula (I) in the same lipid composition administered to the patient.

The present invention additionally relates to a physiologically acceptable lipid composition intended for MRI imaging comprising at least one complex according to the present invention.

It also relates to a composition according to the present invention in the form of an emulsion, of liposomes or of micelles.

Furthermore, it relates to a composition according to the present invention comprising water, a dispersed lipid phase, optionally a fluorocarbon and at least one complex according to the present invention.

According to one implementation, these transporters are associated, on the one hand, with at least one chelate of formula (I) and, on the other hand, with at least one specific targeting biovector for the diagnosis of a pathology, in particular in the fields of cancerous diseases, inflammatory and neurodegenerative diseases and cardiovascular diseases.

Use may in particular be made of the following compounds:

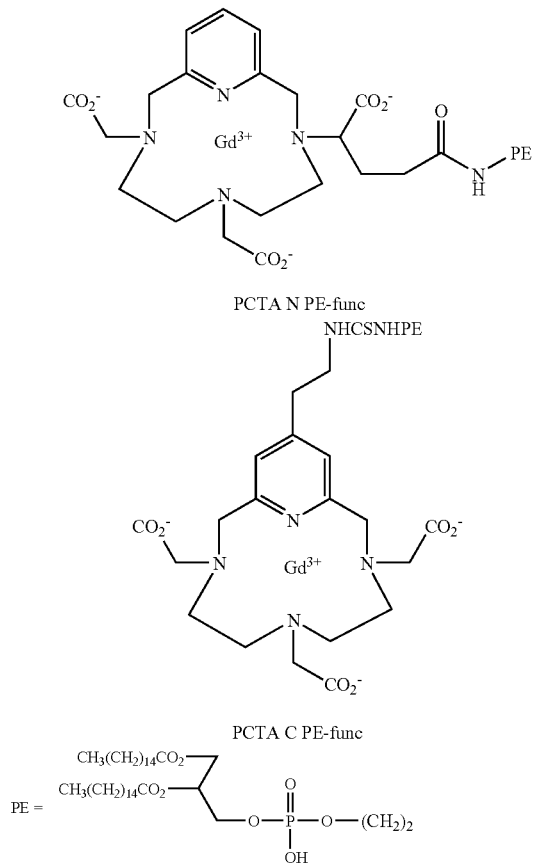

The term "lipophilic chelate" is understood to mean that the chelate has been chemically modified so as to exhibit a lipophilicity (a sufficiently high lipophilicity or, conversely, a sufficiently low hydrophilicity) such that it can be associated with the lipophilic transporter so as to form a lipid composition sufficiently stable for satisfactory diagnostic use.

The paramagnetic metals include the lanthanides of atomic number 58-70 and the transition metals of atomic number 21-29, 42 or 44, for example scandium, titanium, vanadium, chromium, manganese, iron, cobalt, nickel, copper, molybdenum, ruthenium, cerium, praseodymium, neodymium, promethium, samarium, europium, gadolinium, terbium, dysprosium, holmium, erbium, thulium, and ytterbium. Preference is particularly given to the elements Gd(III), Mn(II), europium, dysprosium. The radionuclides include the radioactive forms of the elements Sm, Ho, Y, Pm, Gd, La, Lu, Yb, Sc, Pr, Tc, Re, Ru, Rh, Pd, Pt, Cu, Au, Ga, In, Sn, Cr and Pb.

According to one implementation, as in the document US 20040248856, use is made, as lipophilic group of the chelate of formula (I) of the phosphoglycerides typically resulting from lecithins in which the $R_5COO$ groups are fatty acids, such as oleic acid, palmitic acid or stearic acid. Use may also be made of the phosphoglycerides where $R_5$ is a saturated or unsaturated and optionally substituted hydrocarbyl group. The hydrocarbyl group typically comprises at least 6, preferably at least 10, carbon atoms for sufficient lipophilicity. The $R_5$ group can include one or more cyclic groups.

Use is or is not made of a spacer group, it being possible for the spacer to include a portion resulting from the phosphoglyceride, for example a $CH_2CH_2$ group resulting from a phosphodiglyceride of phosphatidylethanolamine type. Depending on the implementations, the spacer includes portions derived from peptides, pseudopeptides, sequences of amino acids, polyalkylene glycols, in particular polyethylene glycol PEG, and analogous products.

The compounds of formula (I) in the form of complexes according to the present invention are included in compositions comprising lipophilic transporters, these compositions being provided in the form of particles, lipophilic at least at the surface, suspended in an aqueous or hydrophilic medium. These particles are nanoparticles with a diameter of the order of 10 nm to 500 nm, preferably 10 to 100 nm, indeed even 10 to 50 nm.

Mention will be made, as possible particles, of liposomes, which may unilamellar or multilamellar, micelles, oil droplets, lipoproteins, such as HDL, LDL, IDL, VLDL, chylomicrons, fluorocarbon nanoparticles, nanobubbles or analogous products, the surface of which is lipophilic.

Per particle, the chelate number is of the order of 20 000 to 100 000 for the nanoemulsions (hydrodynamic diameter >80 nm), of the order of 200 to 15 000 for the liposomes and of the order of 10 to 500 for the micelles.

In the case of lipid transporters of liposome type, they will be prepared, for example, using phospholipids resulting from choline (phosphatidylcholines), serine (phosphatidylserines), glycerol (phosphatidylglycerols), ethanolamine (phosphatidylethanolamines) or inositol (phosphatidylinositol). The fatty acids used will, for example, be aliphatic chains comprising 10 to 24 carbon atoms. Use will in particular be made of the following fatty acids: lauric acid, myristic acid, palmitic acid, stearic acid, oleic acid or linoleic acid, in particular saturated fatty acids. Mention will be made, among the known phospholipid derivatives which can be used, of the following: (DLPC), (DMPC), (DPPC), (DAPC), (DSPC), (DOPC), (DPDPC), (PMPC), (DLPG) or (DPPG). Use can also be made of phosphatidylethanolamines and their derivatives with PEGs of varied molecular weights (300 to 5000 daltons), such as DPPE-PEG (DSPE-PEG), for example DPPE-PEG2000. Numerous processes for the preparation of liposomes incorporating chelates are known, in particular in WO92/21017. For example, in the case of phospholipids, the phospholipids are dissolved in an organic solvent, the solvent is evaporated under vacuum, to obtain a film of the compounds forming the liposome, and the film is hydrated. The size of the liposome is obtained by various possible techniques, such as sonication, extrusion or microfluidization of the initial liposome suspension. The compounds (I) will be typically incorporated in the lipid biolayer of the liposomes.

For the micelles, use can in particular be made of those described in "Surfactants and Polymers in Drug Delivery", by M. Malmsten, Ch. 2, pp. 19-50, Marcel Dekker Inc., 2002 edition; and in particular micelles based on phospholipids and on PEG-phospholipid derivatives. Use can also be made of associations of micelles and of liposomes as a function of their charges, it being possible for a micelle to comprise several hundred chelate molecules.

Depending on the implementations, these transporters comprise constituents of surfactant type which are of use in particular for the coupling with biovectors by virtue of the appropriate functional groups of the lipid/surfactant constituents (for example phosphatidylethanolamine). Numerous coupling possibilities are restated in US 2004/0248856.

For compositions intended for specific targeting, use may be made of the biovectors restated in particular in the document WO 2004/112839 (in particular pages 60 to 82). Mention will in particular be made of peptides, receptor-specific recognition ligands, vitamin derivatives, in particular for the targeting of integrins, fibrin, EGF/VEGF receptors. Use may also be made of amphiphilic ligands capable of mixing with components of the micelles or of amphiphilic ligands capable of binding to amphiphilic components of liposomes or micelles. For example, the ligand can bind to amphiphilic components of liposomes or micelles via acid or isothiocyanate functional groups. The ligand can be incorporated during the preparation of the micelles or fixed to preprepared micelles incorporating amphiphilic groups intended to be coupled to the ligand.

According to advantageous implementations for the preparation of lipid nanoemulsions, use is made of liquids of perfluorocarbon type, such as described in U.S. Pat. No. 5,958,371, liquid emulsion comprising nanoparticles comprising a perfluorocarbon with a fairly high boiling point (for example between 50 and 90° C.) surrounded by coating composed of a lipid and/or a surfactant. The surfactant is capable of directly coupling to a targeting biovector or of including an intermediate compound covalently bonded to the biovector, if appropriate using a chemical bonding agent. Use may also be made of a cationic coating, so as to adsorb negatively charged biovectors. Mention will be made, as examples of lipids/surfactants, of phospholipids, fatty acids, cholesterols, lysolipids, sphingomyelins or lipids conjugated to PEGs.

Use will then be made, for example, as phospholipids, of the following compounds: phosphatidylcholine, dioleoylphosphatidylcholine, dimyristoylphosphatidylcholine, dipalmitoylphosphatidylcholine, distearoylphosphatidylcholine or phosphatidyl-ethanolamine.

Use will then be made, for example, of perfluorocarbons chosen from: perfluorodecalin, perfluorooctane, perfluorodichlorooctane, perfluoro-n-octyl bromide, perfluoroheptane and analogous products.

According to advantageous implementations, use will be made, to prepare contrast agents according to the invention, of appropriate methods and lipid compositions, in particular liposomes, micelles or emulsions.

It should be remembered that nanoemulsions are heterogeneous lipid mixtures of lipids appropriately obtained by mechanical stirring and/or addition of emulsifying agents. For example, the chelates, rendered lipophilic, are mixed mechanically with organic solvents, such as chloroform. After evaporating the solvent, the lipids are resuspended in an aqueous medium, such as PBS, in order to obtain an emulsion, which is subsequently typically subjected to sonication and microfluidization. The emulsions obtained can be lyophilized with, if appropriate, use of agglutination inhibitors.

The present invention thus relates to a process for the preparation of a composition according to the present invention comprising:
  the preparation of a mixture comprising a complex according to the present invention and an aqueous phase;
  the stirring of the mixture so as to obtain a homogeneous dispersion of the constituents.

According to another implementation, the emulsions are prepared according to the following process: mixing:
  oily perfluorocarbon phase (approximately 40%)
  water+safflower oil and/or glycerol
  surfactant solution (1 to 10%, preferably 2 to 5%, this solution being a mixture comprising, for example, the lipophilic chelate, cholesterol, a phospholipid such as lecithin, and optionally a biovector). The surfactant solution typically comprises 10 to 50% of chelate or complex according to the invention.
  if appropriate fluorinated surfactant, in particular with a high HLB, such as Pluronic F 68, Sodium Dodecyl Sulfate, Triton or Tween.

Use will very advantageously be made of micelles (lipid monolayers, liposomes being lipid bilayers):
  the size of which can be controlled more easily than that of liposomes, the preferred size of the micelles being of the order of 30 to 300 nm, preferably 50 to 100 nm, which gives them easier access to the tissues than larger particles,
  which can be used with or without incorporation of gases, the gases being of use in particular in ultrasound imaging but not necessarily in MRI,
  which can comprise an oily phase which does not present a stability problem, so as to be stable for several months.

Furthermore, in the case of the micelles, the chelates are more easily disposed at the external periphery of the monolayer, which is advantageous if it is desired to avoid incorporation of chelates inside the sphere formed by the micelle and to optimize the signal for a given amount of chelates of the composition.

Use is typically made, to formulate the emulsion formed of desired paramagnetic contrast agent, of 1 to 75% by weight of lipophilic chelate compound or of complex according to the invention with respect to the total ingredients of the emulsion. The composition forming the contrast agent is preferably administered intravascularly, depending on the patient examined, for example in a proportion of 0.1 mg to 1 g of lipophilic chelate compound and of 1 to 50 micromol of paramagnetic metal ion per kg of patient.

The lipid compositions obtained are, if appropriate, formulated using additives, in particular for administration by intravenous injection. Mention will in particular be made of dextrose, sodium chloride or antimicrobial agents.

Advantageously, by virtue of the compositions according to the invention, it is possible to obtain an increase in the relativity per ion. Relaxivities r1 of the order of 10 to 30 $s^{-1}Gd^{-1}$, indeed even more, at fields of 0.5 to 1.5 T approximately are typically obtained. The appropriate coupling of chelates of formula (I) or of complexes according to the invention with the particles is intended to obtain an association of a very high number of chelates, of the order of 2000 to 100 000 chelates per particle, typically of 10 000 to 50 000 chelates. It is thus possible to obtain particles, the main characteristics of which are, for example, as follows, it being possible for these characteristics to vary according to the precise compositions of the emulsions, their process of preparation and the nature of the biovector:

polydispersity index: 0.2 to 0.3;

$[Gd^{3+}]$=2 to 10 mM, preferably 3 to 7 mM;

concentration of particles: 50 to 100 nM;

r1 $(mM^{-1}s^{-1}Gd^{-1})$: 5 to 40, preferably 10 to 40;

r2 $(mM^{-1}s^{-1}Gd^{-1})$: 20 to 40;

r1 $(mM^{-1}s^{-1}particle^{-1})$: $10^6$ to $4\times10^6$;

number of biovectors: 50 to 1000, in particular 100 to 300;

In addition to the PCTA derivatives, the Applicant has also studied:

lipophilic chelates of TRITA PE and GdP8A-PE type

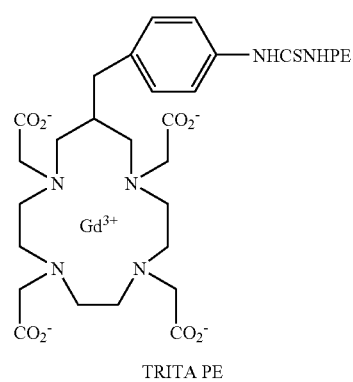

TRITA PE

-continued

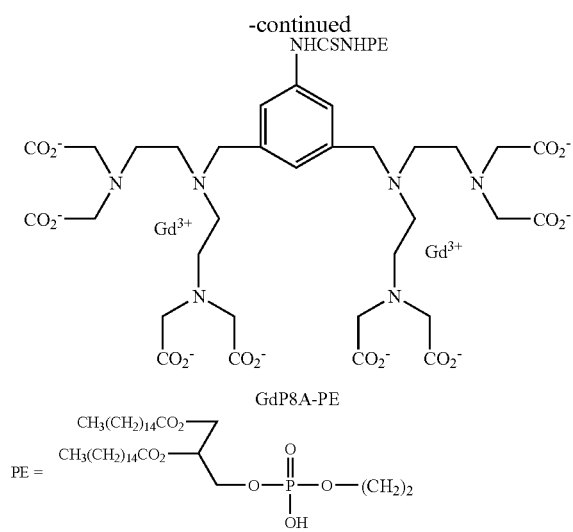

GdP8A-PE

PE = 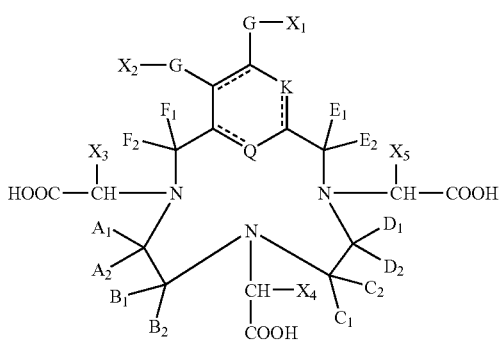

lipophilic chelates comprising at least one lipophilic portion coupled to other chelates, for example chosen from the following:

chelates derived from DO3A, including HDD-DO3A, such as described in the documents: Magnetic Resonance Materials in Physics, Biology and Medicine, 12, 2001, 114-120; J. Chem. Soc., Perkin Trans., 2, 2001, 929-933; Academic Radiology, vol. 9, suppl. 1, 2002; Chem. Eur. J., 1995, 10, 2977-2983 chelates described in the documents WO 2004/087656, WO 03/008390, US 2003/171561 (Tweedle), U.S. Pat. No. 6,719,958, US 2002/090342 and U.S. Pat. No. 6,517,814.

The invention also relates to the lipid compositions comprising, in association, at least one chelate of formula (I) and at least one lipophilic chelate of the prior art cited in the patent application. Furthermore, use may be made of several different biovectors in the same diagnostic composition, for example when several different biovectors are capable of targeting the same pathology.

The invention also relates to the intermediate compounds of formula (II) for the preparation of a compound of formula (I)

(II)

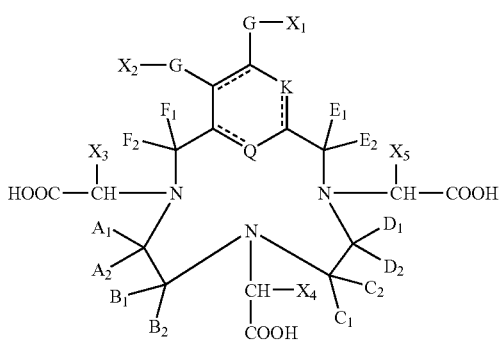

in which:
1) ═ represents a single or double bond;
2) $A_1, A_2, B_1, B_2, C_1, C_2, D_1, D_2, E_1, E_2, F_1, F_2$, Q, K and $R_7$ have the same meaning as in the preceding claims, G is not present and $X_1, X_2, X_3, X_4$ or $X_5$, which are identical or different, independently represent $(CH_2)_a$—$NH_2$ or $(CH_2)_a$—$NO_2$ or

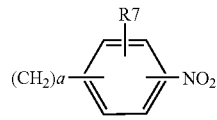

with a=1, 2 or 3,
or $A_1, A_2, B_1, B_2, C_1, C_2, D_1, D_2, E_1, E_2, F_1, F_2$, Q, K and $R_7$ have the same meaning as in the preceding claims, G represents O or $NHR_4$, in which $R_4$ has the same meaning as in the preceding claims, and $X_1, X_2, X_3, X_4$ or $X_5$, which are identical or different, independently represent $(CH_2)_a$—$CO_2H$ or

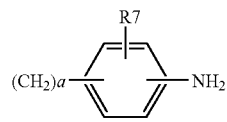

or $(CH_2)_a$—$NH_2$ or $(CH_2)_a$—$NO_2$ or

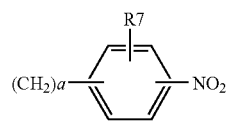

with a=1, 2 or 3.

Advantageously, $X_1$ or $X_2$, which are identical or different, independently represent $(CH_2)_a$—$CO_2H$ or $(CH_2)_a$—$NH_2$ or $(CH_2)_a$—$NO_2$.

Other aspects of the invention are illustrated in the following examples, it being known that the compounds of Examples 5, 6, 7, 8, 10, 17, 18, 19, 20, 21 and 22 are lipophilic chelates carrying a lipophilic chain according to the invention.

EXAMPLE 1 a) N,N''-Bis(o-nitrophenylsulphonyl)diethylenetriamine

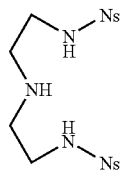

8.4 g of NaOH are dissolved in 100 ml of $H_2O$ at 0° C. and 9.2 g of diethylenetriamine are added, followed dropwise, at 0° C., to a solution of 41.5 g of 2-nitrophenylsulphonic acid chloride dissolved in 100 ml of tetrahydrofuran. The reaction medium is taken up in $CH_2Cl_2$ and the organic phase is washed with $H_2O$ and then dried over magnesium sulphate. After evaporating the solvent, 37.5 g of crystals are obtained.

m/z: ES+ 474.7 b) N,N''-Bis(2-nitrophenylsulphonyl)-N'-(t-butoxycarbonyl)diethylenetriamine

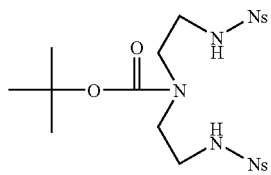

18 g of di(tert-butyl) carbonate are added portionwise to a solution comprising 32.4 g of compound obtained in stage a) in a mixture of 97 ml of 2N aqueous NaOH solution and 225 ml of $CH_3CN$.

After stirring at 25° C. for 3 h, the reaction medium is evaporated to dryness and the residue is taken up in 400 ml of $CH_2Cl_2$. The organic phase is washed twice with 100 ml of $H_2O$.

After drying over magnesium sulphate and then concentrating the organic phase, the residue obtained is purified by chromatography on a column (d=15 cm) comprising 1 kg of silica (Merck® 40-63 μm), elution being carried out with a $CH_2Cl_2/CH_3COCH_3$ mixture, gradient from 99/1 to 90/10 (v/v).

After evaporating the solvent, 28.5 g of product are obtained.

m/z: ES− 572.5 c) tert-Butyl ester of 3,9-bis(2-nitrobenzenesulphonyl)-3,6,9,15-tetraaza-bicyclo[9.3.1]pentadeca-1(14),11(15),12-triene-6-carboxylic acid

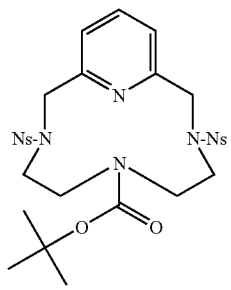

A solution comprising 28 g of the compound obtained in stage b) in 210 ml of $CH_3CN$ in the presence of 41.4 g of calcined $K_2CO_3$ is brought to reflux for 1 h 30. After addition of 11 g of 2,6-bis(chloromethyl)pyridine, the mixture is heated at reflux overnight.

The precipitate formed is filtered off, washed with 1 l of water and then dried under vacuum; w=26.8 g.

m/z: ES+ 677.8 d) tert-Butyl ester of 3,6,9,15-tetraazabicyclo[9.3.1]pentadeca-1(14),11(15),12-triene-6-carboxylic acid

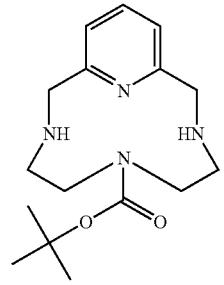

16 g of LiOH are added to 20 g of the compound obtained in stage c) in suspension in 310 ml of dimethylformamide and then 18 g of thioglycolic acid are added dropwise over ½ h.

The reaction medium, coloured red, is stirred at 25° C. for 6 h and then 400 ml of $H_2O$ and 400 ml of $CH_2Cl_2$ are added thereto. After stirring and separating by settling, the aqueous phase is separated and extracted with 400 ml of $CH_2Cl_2$. This organic phase, after washing twice with water, is combined with the preceding phase and the combined product is concentrated. The oily residue is purified by flash chromatography on silica (Merck®, 40-63 μm), elution being carried out with a $CH_3OH/NH_4OH$ (50/1) mixture after removing the impurities by elution with $CH_3OH$.

After evaporating the conforming fractions, 5.5 g of the product are obtained.

m/z: ES+ 307.6 e) tert-Butyl ester of 3,9-bis(ethoxycarbonylmethyl)-3,6,9,15-tetraazabicyclo-[9.3.1]pentadeca-1(14),11(15),12-triene-6-carboxylic acid

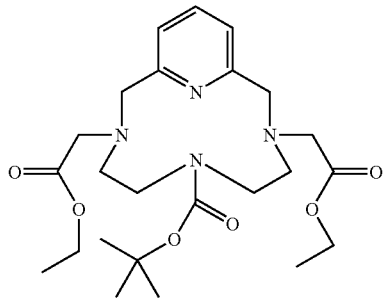

9.6 g of ethyl bromoacetate and 11 g of calcined $K_2CO_3$ are added to a solution of 8 g of compound obtained in stage d) in 60 ml of $CH_3CN$ and 26 ml of diisopropyl ether and then the mixture is brought to its reflux temperature for 24 h.

After filtering and then evaporating under vacuum, the oil obtained is purified by flash chromatography on silica (Merck®, 40-63 μm), elution being carried out with a heptane/ethyl acetate (60/40 v/v) mixture.

After evaporating, 6 g of oil are obtained.

m/z: ES+ 479.4 f) Ethyl ester of (9-ethoxycarbonylmethyl-3,6,9,15-tetraazabicyclo[9.3.1]pentadeca-1(15),11,13-trien-3-yl)acetic acid

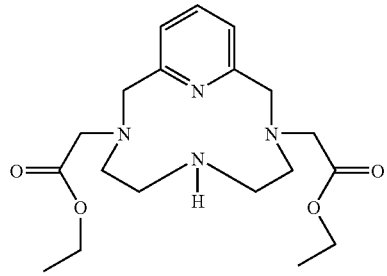

5 g of the compound obtained in stage e) are dissolved in 30 ml of trifluoroacetic acid and the mixture is stirred at 25° C. for 1 h 30.

After concentrating the reaction medium under vacuum, the oil obtained is purified by flash-chromatography on silica (Merck®, 40-60 µm), elution being carried out with a $CH_2Cl_2/CH_3OH$ (97/3, v/v) mixture.

After removing the solvent, 3 g of the solid product are obtained.

m/z: ES+ 379.5 g) Methyl ester of 2-(3,9-bis(ethoxycarbonylmethyl)-3,6,9,15-tetraazabicyclo-[9.3.1]pentadeca-1(14),11(15),12-trien-6-yl)-4-(4-nitrophenyl)butyric acid

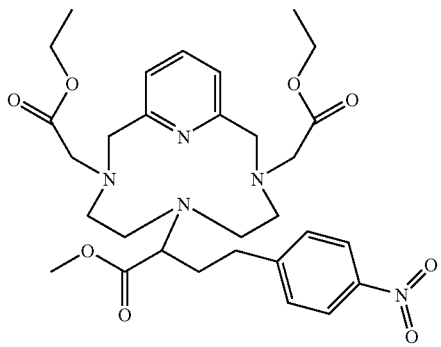

3.6 g of the methyl ester of 2-bromo-4-(4-nitrophenyl) butyric acid are added to a suspension of 3 g of the compound obtained in stage f) in 30 ml of diisopropyl ether and 65 ml of $CH_3CN$ in the presence of 2.5 g of calcined $K_2CO_3$.

After stirring at 85° C. for 48 h, the reaction medium is filtered and concentrated under vacuum, and the residual oil is purified by chromatography on a silica column (Merck® 40-60 µm), elution being carried out with a $CH_2Cl_2$/acetone (70/30 v/v) mixture.

After concentrating to dryness, 2 g of product are obtained.

m/z: ES+ 600.5 h) 2-(3,9-Bis(carboxymethyl)-3,6,9,15-tetraazabicyclo[9.3.1]pentadeca-1(14),11(15),12-trien-6-yl)-4-(4-nitrophenyl)butyric acid

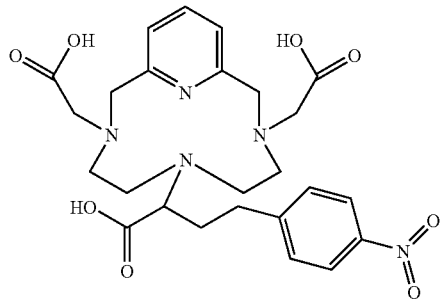

2 g of the compound obtained in stage g) are added to a solution of 10 ml of 12N HCl and then the mixture is stirred at its reflux temperature for 48 h.

After filtering and concentrating, the residue is purified by chromatography on silanized silica gel (Merck® 0.063-0.20 µm), elution being carried out with an $H_2O/CH_3OH$ mixture, to give 1.5 g of product.

m/z: ES− 528.4 i) Gadolinium complex of 2-(3,9-bis(carboxymethyl)-3,6,9,15-tetraazabicyclo[9.3.1]pentadeca-1(14),11(15),12-trien-6-yl)-4-(4-nitrophenyl)butyric acid

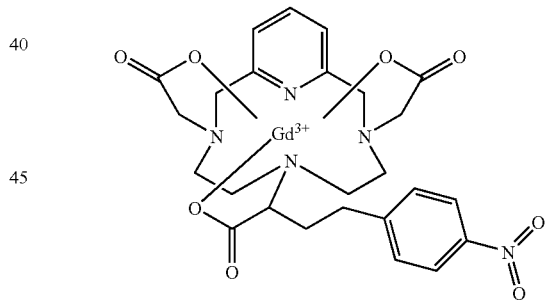

1 g of the compound obtained in stage h) is introduced into 40 ml of $H_2O$.

The pH of the suspension is brought to 5 by addition of a 2N aqueous NaOH solution and then the medium is heated at 50° C. until dissolution is complete.

After addition of 350 mg of $Gd_2O_3$, the solution, still maintained at pH 5 by addition of a 2N aqueous NaOH solution, is heated at 80° C. for 6 h.

After filtering off the salts by evaporation, the residue is recrystallized from ethanol; the precipitate is dissolved in water and treated with a Chelex® 100 resin (Bio-Rad). After precipitating from ethanol, the precipitate is filtered off and dried. w=1.2 g.

m/z: ES− 682.9 j) Gadolinium complex of 4-(4-aminophenyl)-2-(3,9-bis(carboxymethyl)-3,6,9,15-tetraazabicyclo[9.3.1]pentadeca-1(14),11(15),12-trien-6-yl)butyric acid

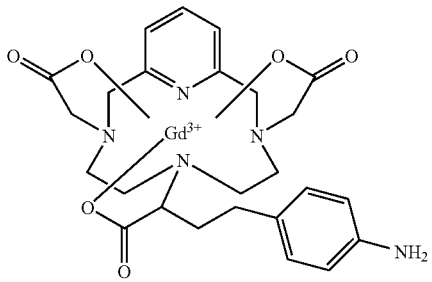

0.4 g of 10% palladium-on-charcoal catalyst is added to 1 g of the compound obtained in stage i) dissolved in 50 ml of H₂O and then the reaction medium is stirred at 25° C. under a hydrogen pressure of 3×10⁵ Pa for 6 h. After removing the catalyst by filtration through a Millipore® filter (0.45 µm and 0.22 µm), the solution is evaporated to give 0.8 g of product.

m/z: ES+ 654.9

EXAMPLE 2 a) Methyl ester of 4-(4-nitrophenyl)-2-(3,6,9,15-tetraazabicyclo[9.3.1]pentadeca-1(14), 11(15),12-trien-3-yl)butyric acid

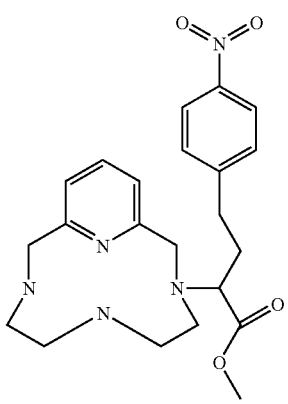

A solution of 102 g of the ester methyl 2-bromo-4-(nitrophenyl)butyrate in 100 ml of CH₃CN is added to a suspension of 70 g of 3,6,9,15-tetraazabicyclo[9.3.1.]-pentadeca-1(15), 11,13-triene in 800 ml of CH₃CN in the presence of 910 ml of anion-exchange resin in the strong base form (Amberlite® IRA458).

After stirring at 25° C. for 3 days, filtering off the resin and evaporating, the oil obtained is purified by chromatography on a column of 5 kg of silica (Merck®, 40-60 µm), elution being carried out with a CH₂Cl₂/CH₃OH (70/30 v/v) mixture. 38 g of product are obtained.

m/z: ES+ 428.6 b) Methyl ester of 2-(6,9-bis(ethoxycarbonylmethyl)-3,6,9,15-tetraazabicyclo-[9.3.1]pentadeca-1(14),11(15),12-trien-3-yl)-4-(4-nitrophenyl)butyric acid

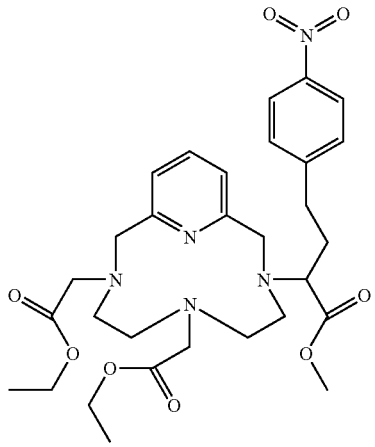

5 g of K₂CO₃ and 4.3 g of ethyl bromoacetate are added to a solution of 5 g of the compound obtained in stage a) in 70 ml of CH₃CN and 35 ml of diisopropyl ether and then the mixture is left stirring at reflux for 24 h.

After removing the salts by filtration and concentrating the solution, the oil obtained is purified by chromatography on silica (Merck® 40-63 µm), elution being carried out with a CH₂Cl₂/acetone (70/30 v/v) mixture.

4.9 g of solid product are obtained.

m/z: ES+ 600.6 c) 2-(6,9-Bis(carboxymethyl)-3,6,9,15-tetraazabicyclo[9.3.1]pentadeca-1(14),11(15),12-trien-3-yl)-4-(4-nitrophenyl)butyric acid

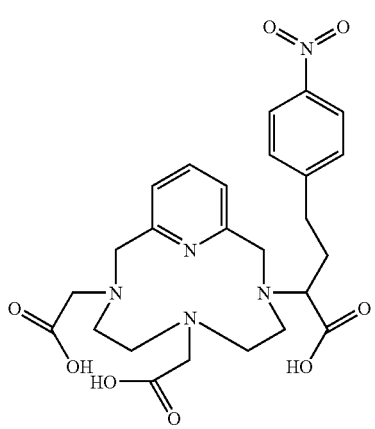

By applying the same procedure as for stage h) of Example 1, 2.8 g of product are obtained from 4 g of the compound obtained in stage b)

m/z: ES− 528.4 .

d) Gadolinium complex of 2-(6,9-bis(carboxymethyl)-3,6,9,15-tetraazabicyclo-[9.3.1]pentadeca-1(14),11(15),12-trien-3-yl)-4-(4-nitrophenyl)butyric acid

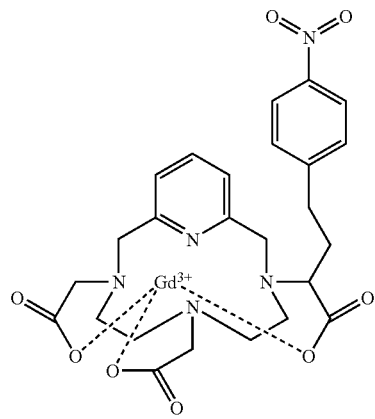

1.4 g of GdCl$_3$.6H$_2$O are introduced into 30 ml of a solution, at pH 5, of 2 g of the compound obtained according to stage c) and the mixture is maintained at 50° C. for 5 h, during which the pH is adjusted by adding an aqueous NaOH solution (2N). The medium is subsequently filtered and then evaporated; 4 g of weakly acidic cation-exchange resin Chelex® 100 (Bio-Rad) are added to the oil obtained dissolved in 40 ml of water.

After stirring at 25° C. for 2 h, the resin is removed by filtration and the solution is evaporated to give 2.3 g of product.

m/z: ES− 682.9 e) Gadolinium complex of 4-(4-aminophenyl)-2-(6,9-bis(carboxymethyl)-3,6,9,15-tetraazabicyclo[9.3.1]pentadeca-1(14),11(15),12-trien-3-yl)butyric acid

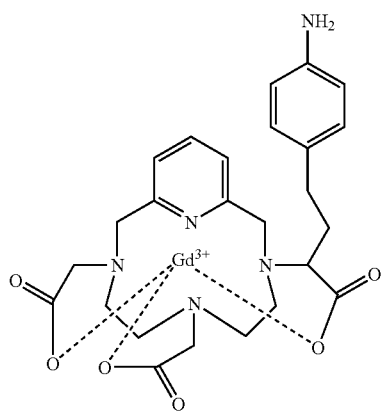

By applying the same procedure as for stage j) of Example 1, 1.8 g of product are obtained from 2 g of the compound obtained in stage d).

m/z: ES+ 654.7

EXAMPLE 3 a) Diethyl ester of 2-(3,9-bis(ethoxycarbonylmethyl)-3,6,9,15-tetraazabicyclo-[9.3.1]pentadeca-1(14),11(15),12-trien-6-yl)pentanedioic acid

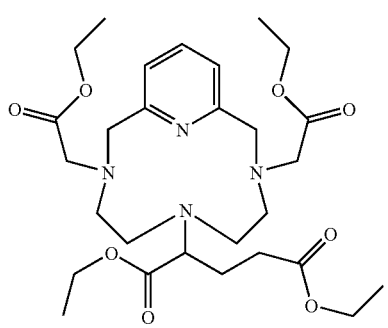

By applying the same procedure as for stage g) of Example 1, 1.2 g of product are obtained, starting with 2 g of compound obtained in stage f) of Example 1) and 3 g of diethyl bromoglutarate, after chromatography on a silica column (Merck® 40-60 µm), elution being carried out with a CH$_2$Cl$_2$/acetone (70/30 v/v) mixture.

m/z: ES+ 565.5 b) 2-(3,9-Bis(carboxymethyl)-3,6,9,15-tetraazabicyclo[9.3.1]pentadeca-1(14),11(15),12-trien-6-yl)pentanedioic acid

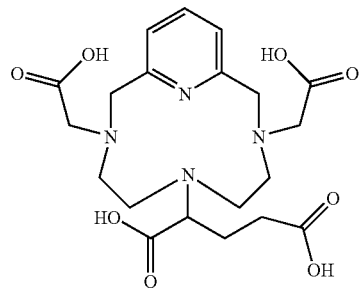

By applying the same procedure as for stage h) of Example 1, 1.7 g of product are obtained from 3 g of the compound obtained in stage a), after chromatography on silanized silica.

m/z: ES− 451.6 c) Gadolinium complex of 2-(3,9-bis(carboxymethyl)-3,6,9,15-tetraaza-bicyclo-[9.3.1]pentadeca-1(14),11(15),12-trien-6-yl)pentanedioic acid

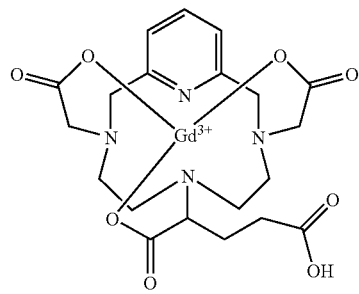

By applying the same procedure as for stage i) of Example 1, 1.2 g of product are obtained from 1 g of the compound obtained in stage b).
m/z: ES− 605.5

EXAMPLE 4 a) 3-Hydroxy-2,6-bis(hydroxymethyl)pyridine

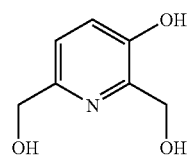

71.1 g (0.75 mol) of 3-hydroxypyridine are dissolved in 300 ml of a 10% aqueous NaOH solution. The combined mixture is brought to 90° C. and then 7×60 ml of a 30% formaldehyde solution are introduced portionwise (5.1 mol). The mixture is left at ambient temperature overnight and then neutralized with $CH_3COOH$. It is concentrated and the residue is taken up in 600 ml of DMF. The insoluble light material is separated. The liquors are acidified with 75 ml 10N HCl. The mixture is concentrated. The residual oil is purified by chromatography on silanized silica with elution with water. Crystals are obtained. w=47 g.
m/z: ES+ 155 b) 3-Benzyloxy-2,6-bis(hydroxymethyl)pyridine

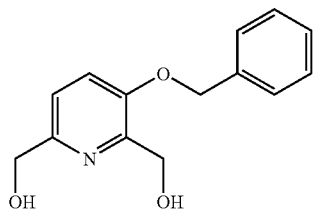

47 g (0.3 mol) of 3-hydroxy-2,6-bis(hydroxymethyl)pyridine are dissolved in 800 ml of acetonitrile. 104 g of $K_2CO_3$ (0.753 mol) and 55 ml of benzyl bromide (0.45 mol) are added. The combined mixture is brought to reflux for 12 h. After having filtered off the insoluble material, the solution is concentrated and the residue is hardened in isopropyl ether. w=39 g.
m/z: ES+ 245 c) 3-Benzyloxy-2,6-bis(bromomethyl)pyridine

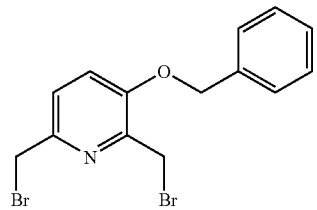

85 g (0.347 mol) of 3-benzyloxy-2,6-bis(hydroxymethyl)pyridine are dissolved in 1000 ml of acetonitrile. The solution is cooled to 5° C. and 419 g of $CBr_4$ and 336 g of triphenylphosphine (1.28 mol) are added while maintaining the temperature at 5° C. After reacting at AT for 6 h, the insoluble material is filtered off and the liquors are concentrated. The product is purified by chromatography on silica with elution with dichloromethane. White crystals are obtained.
m/z: ES+ 371 d) N,N',N''-Tris(2-nitrobenzenesulphonyl)diethylenetriamine

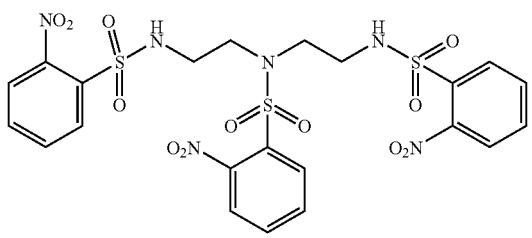

17 g (0.165 mol) of diethylenetriamine are added to a solution of 84 ml of triethylamine in 1000 ml of dichloromethane. The combined mixture is cooled to 0° C. A solution of 120 g (0.544 mol) of 2-nitrobenzenesulphonyl chloride dissolved in 300 ml of dichloromethane is then added dropwise while maintaining the temperature at 0° C. The temperature is slowly allowed to return to AT over 3 h. The mixture is subsequently washed with water and the organic phase is dried and then concentrated. A white powder is obtained.
m/z: ES+ 658 e) 12-Benzyloxy-3,6,9-tris(2-nitrobenzenesulpho-nyl)-3,6,9,15-tetraazabicyclo-[9.3.1]pentadeca-1(14),11(15),12-triene

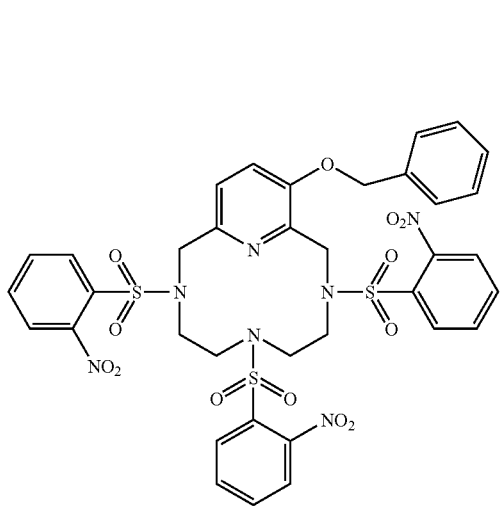

24 g (0.058 mol) of N,N',N''-tris(nosyl)diethylenetriamine are added with efficient stirring to a solution of 16 g of K₂CO₃ in suspension in 300 ml of acetonitrile. The combined product is brought to reflux for 2 h and then 21.5 g (0.057 mol) of 3-benzyloxy-2,6-bis(bromomethyl)pyridine are introduced. The mixture is maintained at reflux overnight. After filtering off the K₂CO₃ and concentrating the liquors, the product is purified by chromatography on silica with elution by dichloromethane/methanol (9/1). w=25 g.
m/z: ES+ 867 f) 12-Benzyloxy-3,6,9,15-tetraazabicyclo[9.3.1]pentadeca-1(14),11(15),12-triene

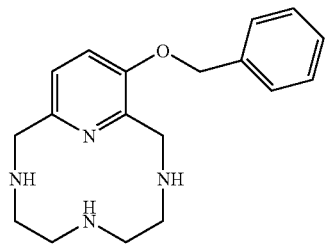

24.2 g (0.0279 mol) of 12-benzyloxy-3,6,9-tris(2-nitrobenzenesulphonyl)-3,6,9,15-tetraazabicyclo[9.3.1]pentadeca-1(14),11(15),12-triene are dissolved in 200 ml of DMF and then 22 g of LiOH and 21 ml of thioglycolic acid are introduced. The combined mixture is left at AT overnight. After evaporating the DMF, the residual oil is taken up in dichloromethane and the organic solution is then washed with water, dried and concentrated. A brown oil is obtained. w=15 g.
m/z: ES+ 312 g) Methyl ester of (12-benzyloxy-6,9-bis(methoxy-carbonylmethyl)-3,6,9,15-tetraazabicyclo[9.3.1]pentadeca-1(14),11(15),12-trien-3-yl)acetic acid

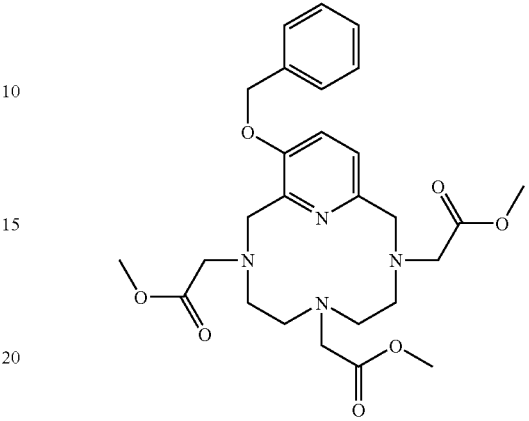

15 g (0.0279 mol) of 12-benzyloxy-3,6,9,15-tetraazabicyclo[9.3.1]pentadeca-1(14),11(15),12-triene are added to a solution of 35 g of K₂CO₃ and 25 ml of methyl bromoacetate in 370 ml of acetonitrile. The combined product is brought to reflux for 18 h. After filtering, the solution is concentrated, the residue is taken up in 200 ml of 1N HCl and the solution is then washed with ether. The aqueous phase is neutralized. It is extracted with dichloromethane and the organic phase is concentrated. A yellow oil is obtained. w=9 g.
m/z: ES+ 522 h) (12-Benzyloxy-6,9-bis(carboxymethyl)-3,6,9,15-tetraazabicyclo[9.3.1]-pentadeca-1(14),11(15),12-trien-3-yl)acetic acid

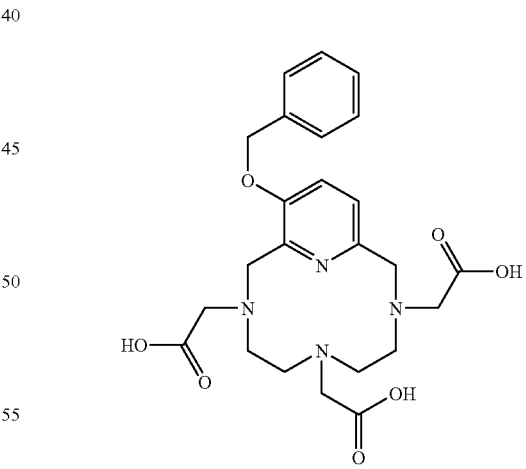

9 g (0.0170 mol) of the methyl ester of (12-benzyloxy-6,9-bis(methoxy-carbonylmethyl)-3,6,9,15-tetraazabicyclo[9.3.1]pentadeca-1(14),11(15),12-trien-3-yl)acetic acid are added to a solution of 50 ml of methanol and 50 ml of 5N NaOH. The combined mixture is brought to reflux for 6 h. After concentrating and neutralizing by passing through IRC50 resin, the product is hardened in isopropanol. White crystals are obtained. w=8 g.
m/z: ES+ 486 i) (6,9-Bis(carboxymethyl)-12-hydroxy-3,6,9,15-tetraazabicyclo[9.3.1]pentadeca-1(14),11(15),12-trien-3-yl)acetic acid

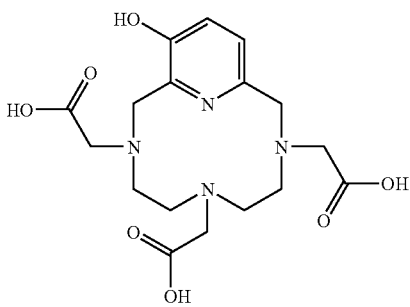

8 g (0.0170 mol) of (12-benzyloxy-6,9-bis(carboxymethyl)-3,6,9,15-tetraazabicyclo[9.3.1]pentadeca-1(14),11(15),12-trien-3-yl)acetic acid are added to 100 ml of 10N HCl. The mixture is left to react overnight at 40° C. It is concentrated. The product is crystallized from acetone. w=6 g.
m/z: ES+ 396 j) Gadolinium complex of (6,9-bis(carboxymethyl)-12-hydroxy-3,6,9,15-tetraazabicyclo[9.3.1]pentadeca-1(14),11(15),12-trien-3-yl)acetic acid

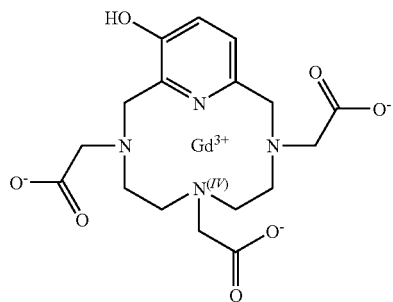

5 g (0.0126 mol) of (6,9-bis(carboxymethyl)-12-hydroxy-3,6,9,15-tetraazabicyclo[9.3.1]pentadeca-1(14),11(15),12-trien-3-yl)acetic acid are dissolved in 80 ml of water. The pH is adjusted to 6 with 2N NaOH and the temperature is brought to 60° C. 2.32 g (0.00631 mol) of $Gd_2O_3$ are added. The combined mixture is stirred at 60° C. for 6 h while maintaining the pH at 6. After filtering off a cloudy material, the solution is concentrated and then the product is hardened in ethanol. White crystals are obtained. w=6.3 g.
m/z: ES+ 550 k) Gadolinium complex of (12-carboxymethoxy-6,9-bis(carboxymethyl)-3,6,9,15-tetraazabicyclo[9.3.1]pentadeca-1(14),11(15),12-trien-3-yl)acetic acid

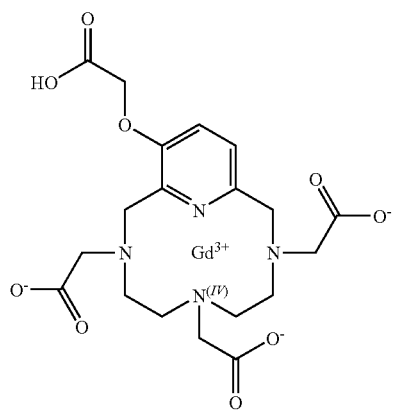

550 mg (0.001 mol) of gadolinium complex of (6,9-bis(carboxymethyl)-12-hydroxy-3,6,9,15-tetraazabicyclo[9.3.1]pentadeca-1(14),11(15),12-trien-3-yl)-acetic acid are added to a solution of 20 ml of water comprising 100 mg (0.005 mol) of NaOH. 180 mg (0.0015 mol) of bromoacetic acid are added. The solution is brought to 50° C. and is left stirring overnight. After concentrating and taking up in ethanol, white crystals are obtained. w=600 mg.
m/z: ES+ 608

EXAMPLE 5 a) Gadolinium complex of the 3-({2-[4-(3,9-bis(carboxymethyl)-3,6,9,15-tetraazabicyclo[9.3.1]pentadeca-1(14),11(15),12-trien-6-yl)-4-carboxybutyryl-amino]ethoxy}hydroxyphosphoryloxy)-2-(octadecanoyloxy)propyl ester of octadecanoic acid

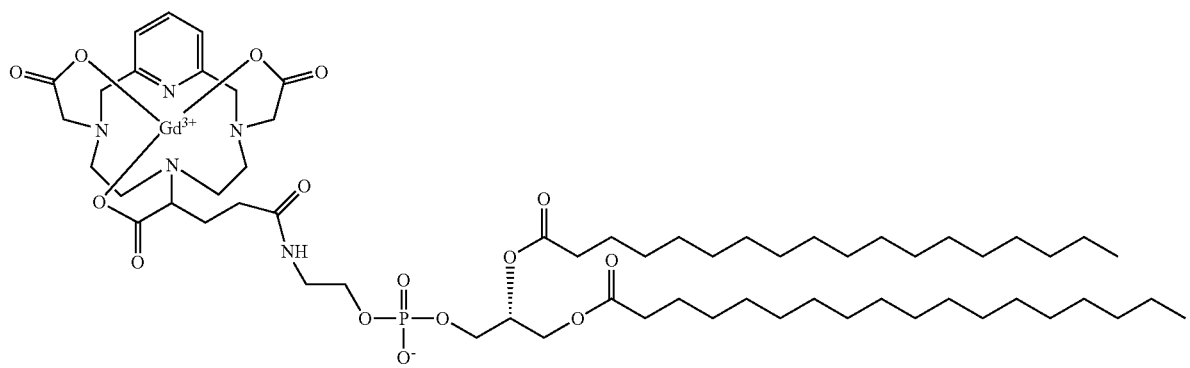

200 mg of the compound obtained in stage c) of Example 3 are dissolved in 10 ml of dimethylformamide. 204 mg of N,N'-dicyclohexylcarbodiimide and 40 mg of N-hydroxysuccinimide are added to this solution. The mixture is stirred at ambient temperature for 1 h and a solution of 250 mg of 1,2-distearoyl-sn-glycero-3-phosphoethanolamine (DSPE, AVANTI® Polar Lipids, Inc.) in 5 ml of pyridine is added. The reaction medium is stirred at ambient temperature for 20 h and then precipitated from 50 ml of ethanol. The product is subsequently purified on silica gel. w=190 mg.

m/z: ES− 1335

EXAMPLE 6 a) Gadolinium complex of 2-(3,9-bis(carboxymethyl)-3,6,9,15-tetraazabicyclo-[9.3.1]pentadeca-1(14),11(15),12-trien-6-yl)-4-(4-octadec-9-enoylamino)-phenyl)butyric acid

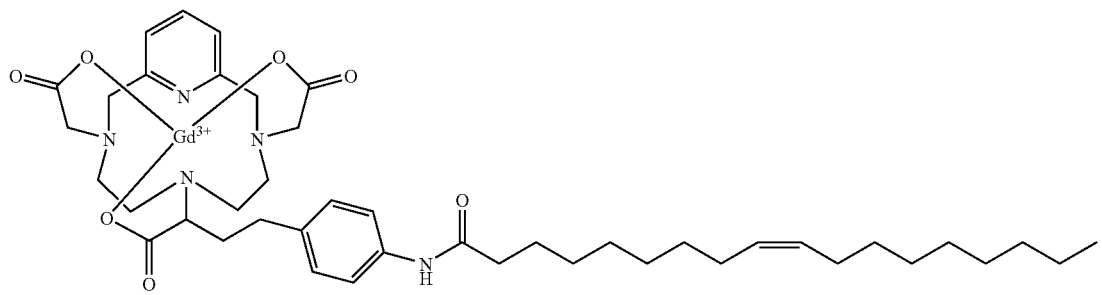

500 g of the compound obtained in stage j) of Example 1 are dissolved in 30 ml of anhydrous DMSO. 230 mg of triethylamine are added, followed by 400 mg of oleoyl chloride (ALDRICH®). The mixture is stirred at ambient temperature for 6 h and precipitated from ethanol. The product is subsequently purified on silica gel. w=300 mg.

m/z: ES− 917

EXAMPLE 7 a) Gadolinium complex of the 2-(6,9-bis(carboxymethyl)-3,6,9,15-tetraazabicyclo[9.3.1]pentadeca-1(14),11(15),12-trien-3-yl)-4-(4-hexadecanoylaminophenyl)butyric acid

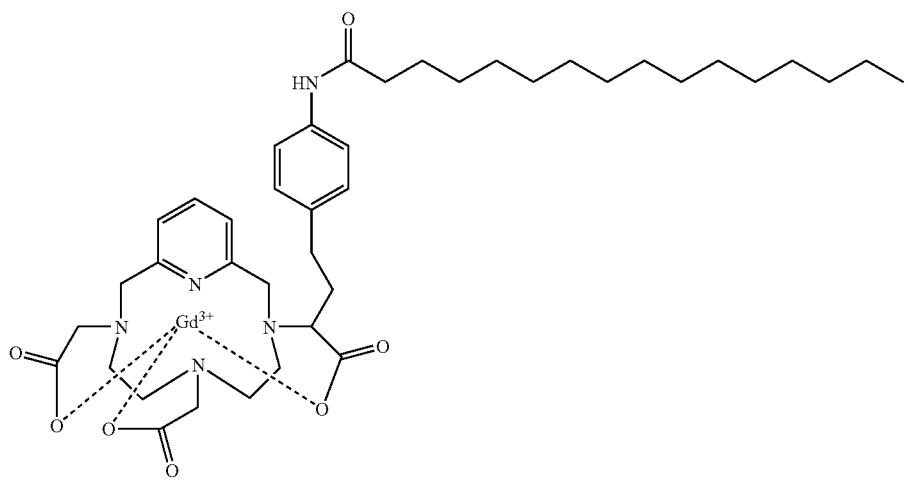

100 mg of compound obtained in stage e) of Example 2 are dissolved in 20 ml of anhydrous DMSO. 50 mg of triethylamine and then 63 mg of palmitoyl chloride (ALDRICH®) are added and the mixture is stirred at ambient temperature for 6 h. After precipitating from ethanol and purifying on silica gel, 56 mg of product are obtained.

m/z: ES− 891

EXAMPLE 8 a) Gadolinium complex of 2-hexadecanoyloxy-3-(hydroxy{2-[2-(3,6,9-tris(carboxymethyl)-3,6,9,15-tetraazabicyclo[9.3.1]pentadeca-1(15),11,13-trien-12-yloxy)acetylamino]ethoxy}phosphoryloxy)propyl ester of hexadecanoic acid

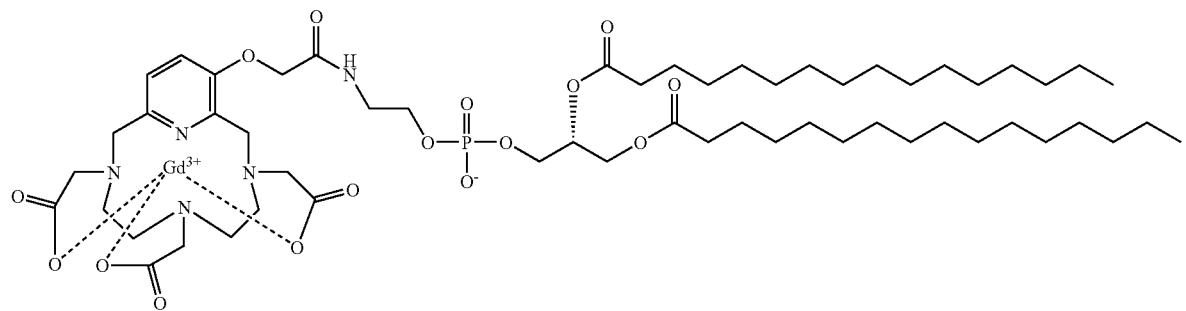

200 mg of the compound obtained in stage k) of Example 4 are dissolved in 20 ml of 1-methyl-2-pyrrolidinone and 500 mg of bromotripyrrolidinophosphonium hexafluorophosphate (PyBroP® ALDRICH®) and then 230 mg of 1,2-dipalmitoyl-sn-glycero-3-phosphoethanolamine (DPPE, AVANTI® Polar Lipids Inc) are added. The reaction medium is stirred at ambient temperature for 24 h and then precipitated from 50 ml of ethanol. After purification on silica gel, 126 mg of product are obtained.

m/z: ES− 1280

EXAMPLE 9 a) Gadolinium complex of 2-(6,9-bis(carboxymethyl)-3,6,9,15-tetraaza-bicyclo[9.3.1]pentadeca-1(14),11(15),12-trien-3-yl)-4-(4-isothiocyanatophenyl)-butyric acid

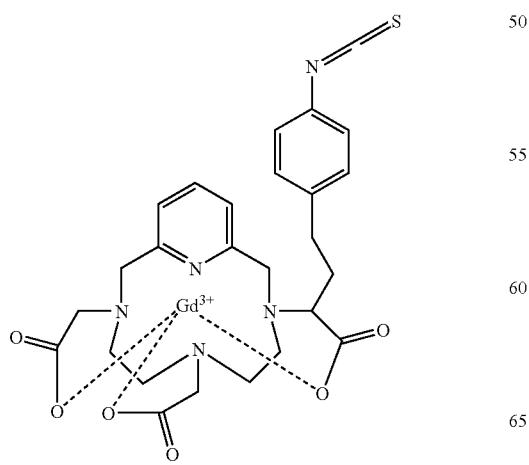

2 g of the product resulting from stage e) of Example 2 are dissolved in a mixture of 24 ml of water and 16 ml of $CHCl_3$. 0.5 ml ($6.5\times10^{-3}$ mol) of thiophosgene is added dropwise and the combined mixture is stirred for 1 h 30 minutes. The reaction medium is separated by settling and the aqueous phase is evaporated under vacuum. The residue is taken up in ethyl ether and stirred overnight at ambient temperature.

The precipitate is filtered off and dried under vacuum. w=2.1 g.

m/z: ES− 695

EXAMPLE 10 a) Gadolinium complex of 2-(6,9-bis(carboxymethyl)-3,6,9,15-tetraazabicyclo-[9.3.1]pentadeca-1(14),11(15),12-trien-3-yl)-4-[4-(3-(octadec-9-enyl)thioureido)phenyl]butyric acid

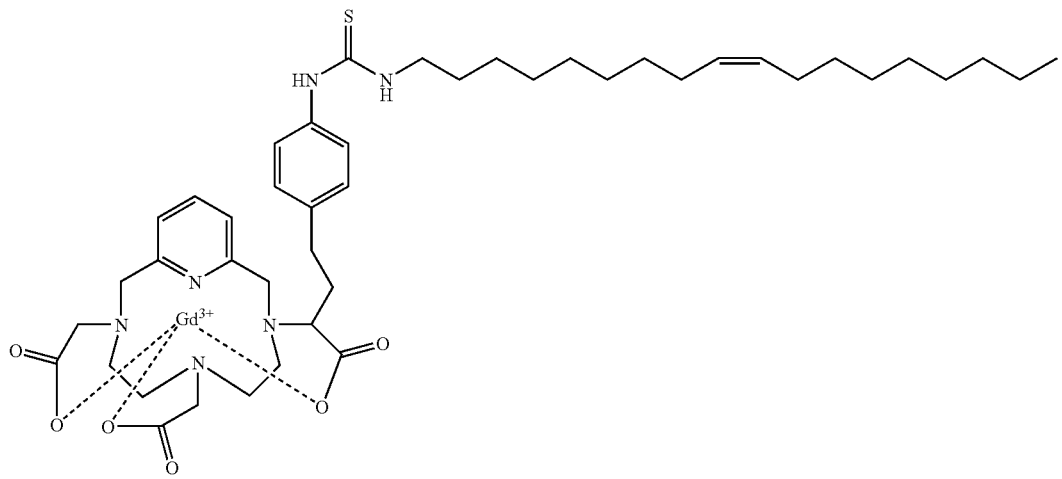

The compound obtained in stage a) of Example 9 (1 g) is dissolved at ambient temperature in 20 ml of DMSO. Oleylamine (550 mg) is subsequently added and the reaction medium is stirred for 48 h before being precipitated from 200 ml of ethyl ether. The precipitate is washed with ethyl ether and then with ethanol. After purifying on silica gel, w=650 mg of product are obtained.

m/z: ES− 962

EXAMPLE 11 a) Ethyl ester of (13-bromo-6,9-bis(ethoxycarbonylmethyl)-3,6,9,15-tetraazabicyclo[9.3.1]pentadeca-1(14),11(15),12-trien-3-yl)acetic acid

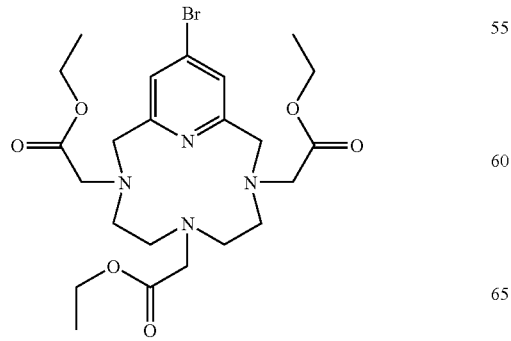

22 g of 13-bromo-3,6,9,15-tetraazabicyclo[9.3.1]pentadeca-1(15),11,13-triene, obtained according to J. Heterocyclic Chem. 27, 1990, pages 167-169, are introduced into 440 ml of CH$_3$CN in the presence of 48 g of calcined K$_2$CO$_3$ and the mixture is maintained at 80° C. for 1 h before the addition of a solution of 50 g of ethyl bromoacetate in 100 ml of CH$_3$CN; the reaction medium is then stirred at 80° C. for 20 h, then cooled to ambient temperature and filtered, and the solvent is evaporated. The residue is taken up in 500 ml of a 1N aqueous HCl solution in the presence of a volume of diethyl ether. After separating the organic phase, the aqueous phase is neutralized with NaHCO$_3$ and then extracted with CH$_2$Cl$_2$. After washing with water and then drying over magnesium sulphate, the organic phase is concentrated and the residue is purified on a silica column (Merck® 500 g, d=10 cm), elution being carried out with CH$_3$COOC$_2$H$_5$. w=20.9 g.
m/z: ES+ 544.6 b) Ethyl ester of [13-(3-tert-butoxycarbonylamino-propenyl)-6,9-bis(ethoxycarbonylmethyl)-3,6,9,15-tetraazabicyclo[9.3.1]pentadeca-1(14),11(15),12-trien-3-yl]acetic acid

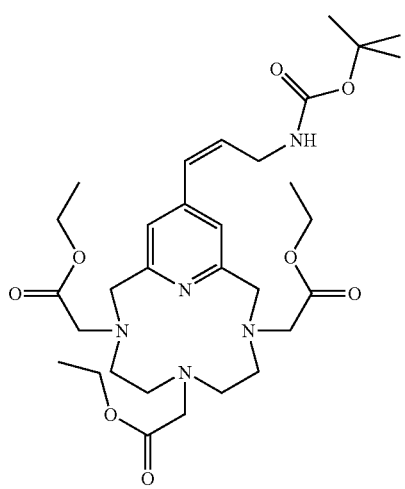

6 g of 3-(tert-butyloxycarbonylamino)propene, 10 ml of triethylamine, then 800 mg of triphenylphosphine and finally 400 mg of palladium acetate are added to a solution of 5 g of the compound obtained in stage a) dissolved in 100 ml of toluene. After heating to 80° C. overnight under an inert atmosphere, the medium is evaporated and the residue is taken up in an aqueous hydrochloric acid solution (pH=1). The aqueous phase is washed with 1 volume of diethyl ether and then of toluene before being brought to pH 6 by addition of NaOH (1N).

After extracting the aqueous solution with CH$_2$Cl$_2$, the organic phase, dried over magnesium sulphate, is evaporated. A brown oil is obtained and is chromatographed on silica gel. w=2.8 g.
m/z: ES+ 621 c) Ethyl ester of [13-(3-tert-butoxycarbonylamino-propyl)-6,9-bis(ethoxycarbonylmethyl)-3,6,9,15-tetraazabicyclo[9.3.1]pentadeca-1(14),11(15),12-trien-3-yl]acetic acid

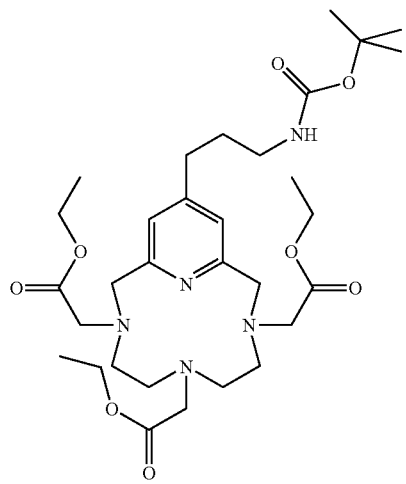

200 mg of 10% palladium-on-charcoal catalyst are added to 2 g of the compound obtained in stage b) dissolved in 80 ml of CH$_3$OH and then the reaction medium is stirred at 20° C. for 2 h 30 under 4×10$^5$ Pa of hydrogen. After filtering through Clarcel®, the solvent is evaporated and 1.8 g of oil are obtained after chromatography on silica gel.
m/z: ES+ 623 d) [13-(3-(tert-Butoxycarbonylamino)propyl)-6,9-bis(carboxymethyl)-3,6,9,15-tetraazabicyclo[9.3.1]pentadeca-1(14),11(15),12-trien-3-yl]acetic acid

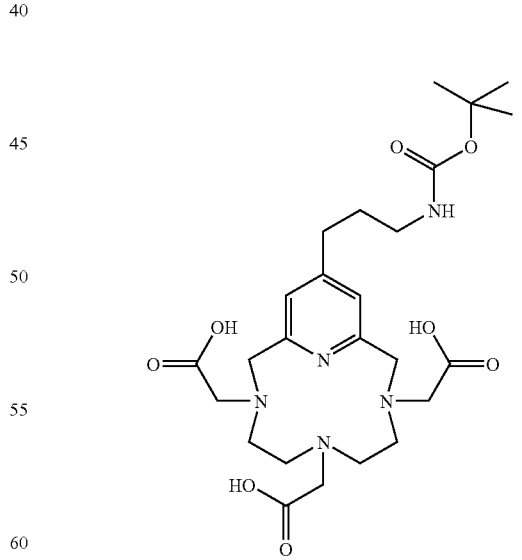

1 g of the compound obtained in stage c), dissolved in 20 ml of a 5N aqueous NaOH solution and 20 ml of CH$_3$OH, is heated at 70° C. for 18 h. After concentrating the reaction medium, the residue is taken up in water and the solution, brought to pH 5.5-6 with a few drops of acetic acid, is concentrated before being purified by chromatography on a column (d=15 cm) comprising 50 g of silanized silica (Merck® 0.063-0.200 µm), elution being carried out with water. After concentrating to dryness, 480 mg of white crystals are obtained.

m/z: ES− 536.5 e) Gadolinium complex of [13-(3-(tert-butoxycarbonylamino)propyl)-6,9-bis(carboxymethyl)-3,6,9,15-tetraaza-bicyclo[9.3.1]pentadeca-1(14),11(15),12-trien-3-yl]acetic acid

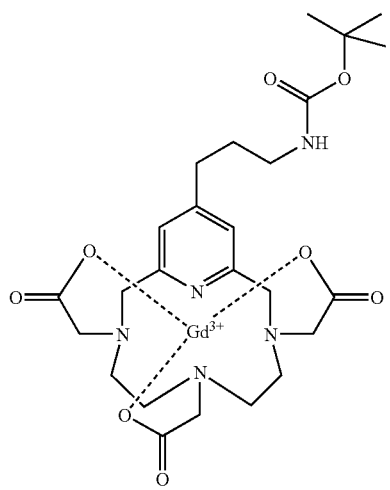

300 mg of the compound obtained in stage d) are dissolved in 10 ml of water, then 100 mg of $Gd_2O_3$ are added all at once and the combined mixture is heated at 60° C. for 3 h 45 min while maintaining the pH between 5.5 and 6 by addition of a 1N aqueous NaOH solution. After filtration, the reaction medium is evaporated and the residue is crystallized from ethanol. After treatment with a Chelex® 100 resin (Bio-Rad), 320 mg of white crystals are obtained.

m/z: ES− 691 f) Gadolinium complex of [13-(3-aminopropyl)-6,9-bis(carboxymethyl)-3,6,9,15-tetraazabicyclo[9.3.1]pentadeca-1(14),11(15),12-trien-3-yl]acetic acid

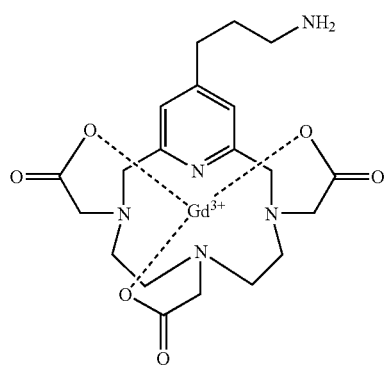

A solution of 300 mg of the complex obtained in stage e) in 18 ml of $CF_3COOH$ is maintained at 25° C. for 3 h before removing the liquid under reduced pressure.

The residue is taken up in diethyl ether and the suspension is filtered. After removing the solvent, the residue is introduced portionwise into a suspension of at least one 1 ml of weak anionic resin (OH⁻) in 5 ml of water; at the end of the addition, the pH, which is stable, must be from 8 to 8.5.

The resin is then separated by filtration, the solvent is removed and the residue is precipitated by addition of ethyl ether. w=200 mg.

m/z: ES+ 593

EXAMPLE 12 a) Gadolinium complex of {6,9-bis(carboxymethyl)-13-[3-(2-ethoxy-3,4-dioxocyclobut-1-enylamino)propyl]-3,6,9,15-tetraazabicyclo[9.3.1]pentadeca-1(14),11(15),12-trien-3-yl}acetic acid

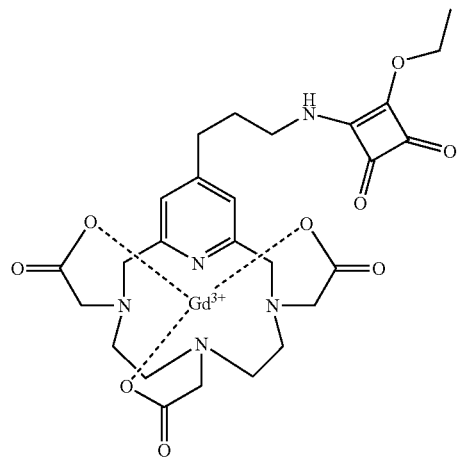

1 g of compound obtained in stage f) of Example 11 is dried with toluene and then suspended in 20 ml of anhydrous DMSO under an argon blanket. 0.4 ml of $Et_3N$, dried over sieves (1.7 eq.), and 720 mg of diethyl squarate (Aldrich, 2.5 eq.) are then added. The mixture is stirred at ambient temperature under an argon blanket for 1 hour. The medium is precipitated from 120 ml of ether. The yellowish oil is washed with ethyl ether. The solid obtained is filtered off and then washed with dichloromethane.

After filtration, 700 mg of a white solid are obtained.

m/z: ES− 718

EXAMPLE 13 a) Benzyl ester of 2-(3,9-bis(ethoxycarbonylmethyl)-3,6,9,15-tetraazabicyclo[9.3.1]pentadeca-1(14),11(15),12-trien-6-yl)-5-(1,3-dioxo-1,3-dihydroisoindol-2-yl)pentanoic acid

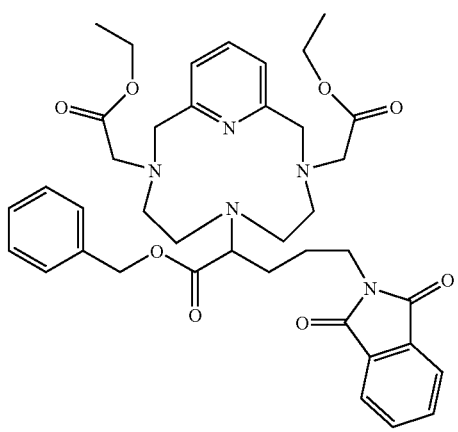

Starting from the compound obtained in stage f) of Example 1 (1 g) and from the benzyl ester of 2-bromo-5-(1,3-dioxo-1,3-dihydroisoindol-2-yl)pentanoic acid (1.5 g) according to the procedure described in stage g) of Example 1. After purification on silica gel, 700 mg of product are obtained.

m/z: ES+ 715 b) 5-Amino-2-(3,9-bis(carboxymethyl)-3,6,9,15-tetraazabicyclo[9.3.1]pentadeca-1(14),11(15),12-trien-6-yl)pentanoic acid

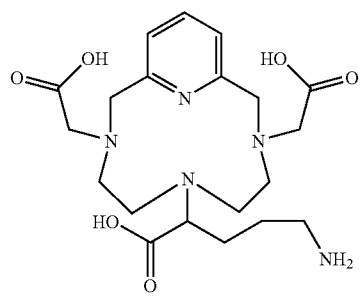

500 mg of product are obtained according to the procedure of stage h) of Example 1 starting from the compound obtained in stage a) (1.6 g).

m/z: ES− 436.5 c) Gadolinium complex of 5-amino-2-(3,9-bis(carboxymethyl)-3,6,9,15-tetraazabicyclo[9.3.1]pentadeca-1(14),11(15),12-trien-6-yl)pentanoic acid

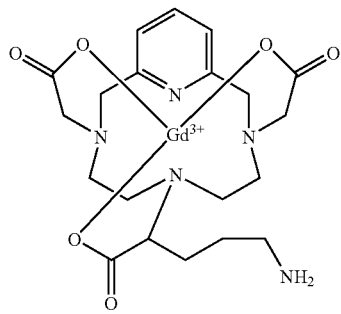

According to the procedure of stage i) of Example 1, starting from 500 mg of the compound obtained in stage b). w=620 mg m/z: ES+ 593

EXAMPLE 14 a) Gadolinium complex of 2-(3,9-bis(carboxymethyl)-3,6,9,15-tetraazabicyclo[9.3.1]pentadeca-1(14),11(15),12-trien-6-yl)-5-(2-ethoxy-3,4-dioxocyclobut-1-enylamino)pentanoic acid

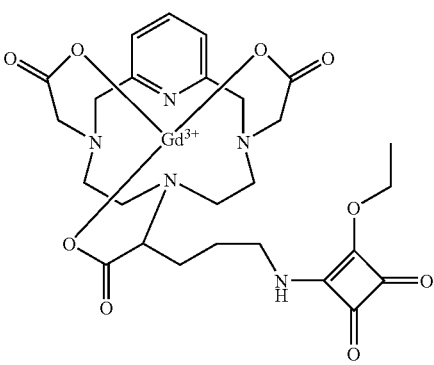

According to the procedure of stage a) of Example 12, starting from 500 mg of the compound obtained in stage c) of Example 13. w=410 mg m/z: ES+ 717

EXAMPLE 15 a) Diethyl ester of 2-bromohexanedioic acid

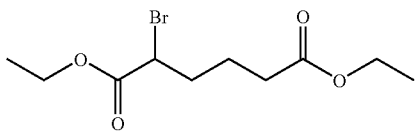

75 g of the monoethyl ester of hexanedioic acid are added to 123 ml of $SOCl_2$ and then brought to reflux for 3 h. 26.4 ml of $Br_2$ are added dropwise while maintaining reflux. The mixture is left overnight at ambient temperature. The solution is poured slowly at 0° C. into 225 ml of ethanol. After addition, the medium is left at 0° C. for 2 h and then poured slowly into 600 ml of ice-cold water. The aqueous phase is extracted with ethyl ether and the ethereal phase is washed with a 10% $NaHCO_3$ solution and then with water. After evaporating the ether, the oil obtained is distilled. w=80 g m/z: ES+ 281 b) Diethyl ester of 2-(3,9-bis(ethoxycarbonylmethyl)-3,6,9,15-tetraazabicyclo-[9.3.1]pentadeca-1(14),11(15),12-trien-6-yl)-hexanedioic acid

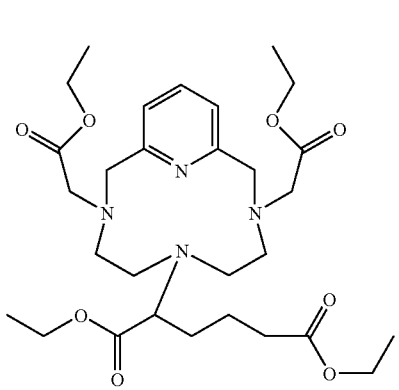

By applying the same procedure as for stage g) of Example 1, 750 mg of product are obtained, starting from 1 g of compound obtained in stage f) of Example 1 and 1.1 g of product obtained in stage a), after chromatography on a silica column (Merck® 40-60 μm), elution being carried out with a $CH_2Cl_2$/acetone (70/30 v/v) mixture.

m/z: ES+ 580 c) 2-(3,9-Bis(carboxymethyl)-3,6,9,15-tetraazabicyclo[9.3.1]pentadeca-1(14),11(15),12-trien-6-yl)hexanedioic acid

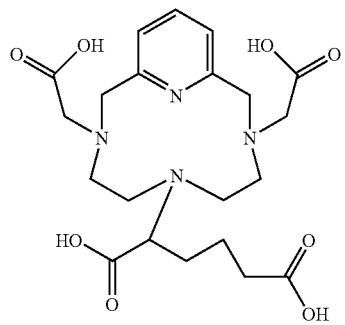

By applying the same procedure as for stage h) of Example 1, 220 mg of product are obtained from 500 mg of the compound obtained in stage b).

m/z: ES– 465 d) Gadolinium complex of 2-(3,9-bis(carboxymethyl)-3,6,9,15-tetraazabicyclo-[9.3.1]pentadeca-1(14),11(15),12-trien-6-yl)-hexanedioic acid

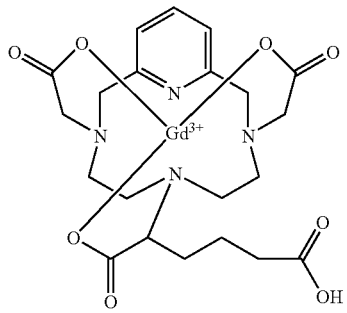

By applying the same procedure as for stage i) of Example 1, 180 mg of product are obtained from 200 mg of the compound obtained in stage c).

m/z: ES– 620

EXAMPLE 16 a) Dimethyl ester of 2-(3,9-bis(ethoxycarbonylmethyl)-3,6,9,15-tetraazabicyclo[9.3.1]pentadeca-1(14),11(15),12-trien-6-yl)but-2-enedioic acid

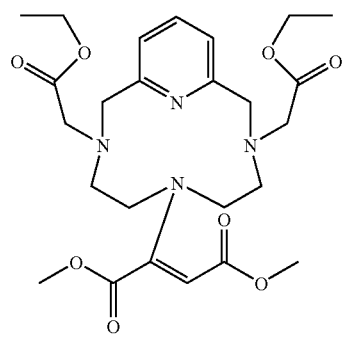

380 mg of dimethyl acetylenedicarboxylate are added to a solution of 500 mg of compound obtained in stage f) of Example 1 in 20 ml of acetonitrile and the mixture is brought to 55° C. for 1 h. After cooling, the solvent is evaporated under reduced pressure and the residual oil is purified on a silica column (Merck® 40-60 μm), elution being carried out with an ethyl acetate/heptane mixture. w=420 mg.

m/z: ES+ 521.6 b) Dimethyl ester of 2-(3,9-bis(ethoxycarbonylmethyl)-3,6,9,15-tetraazabicyclo[9.3.1]pentadeca-1(14),11(15),12-trien-6-yl)succinic acid

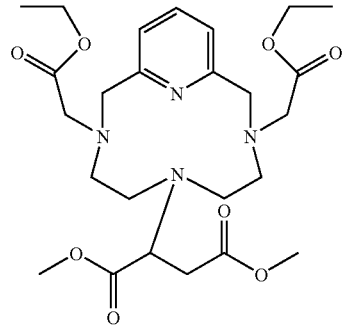

300 mg of NaBH$_3$CN are added to a solution composed of 400 mg of the product obtained in stage a), 10 ml of acetonitrile and 2 ml of acetic acid. The mixture is stirred at ambient temperature for 12 h. The solvent is evaporated under reduced pressure, the residual oil is dissolved in dichloromethane and the solution is washed with aqueous bicarbonate solution until the aqueous wash liquors are neutral. After drying and evaporating the dichloromethane solution, 380 mg of product are obtained.

m/z: ES+ 523.7 c) 2-(3,9-Bis(carboxymethyl)-3,6,9,15-tetraazabicyclo[9.3.1]pentadeca-1(14),11(15),12-trien-6-yl)succinic acid

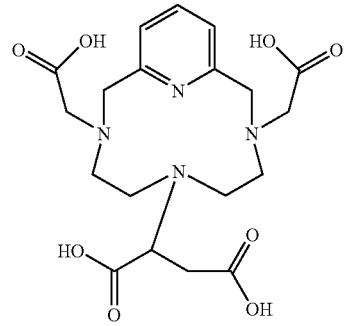

According to the procedure of stage h) of Example 1, starting from 300 mg of product obtained in stage b). w=180 mg m/z: ES− 437 d) Gadolinium complex of 2-(3,9-bis(carboxymethyl)-3,6,9,15-tetraazabicyclo[9.3.1]pentadeca-1(14),11(15),12-trien-6-yl)succinic acid

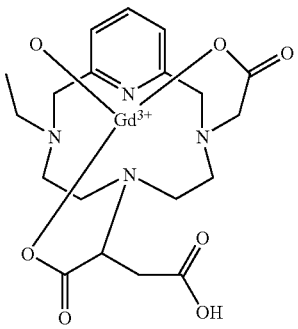

According to the procedure of stage i) of Example 1 starting from 150 mg of compound obtained in stage c). w=170 mg m/z: ES− 591.5

EXAMPLE 17 a) Octadecylamine 2 g of oleylamine in 120 ml of ethanol are hydrogenated at 30° C. under 8 bar of hydrogen in the presence of palladium-on-charcoal. After reacting for 4 h and evaporating the solvent, 1.6 g of product are obtained in the form of a white powder.

m/z: ES+ 270.7 b) 2-(3,9-Bis(carboxymethyl)-3,6,9,15-tetraazabicyclo[9.3.1]pentadeca-1(14),11(15),12-trien-6-yl)-N-octadecylsuccinamic acid

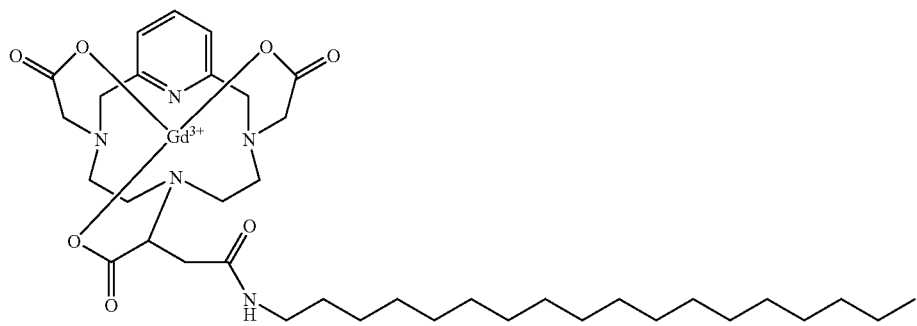

50 mg of the amine prepared in stage a), 70 mg of DCC (dicyclohexylcarbodiimide) and 50 µl of triethylamine are added to a solution of 100 mg of the compound prepared in stage d) of Example 16 in 10 ml of DMF. The medium is stirred at ambient temperature for 18 h and then precipitated from According to the procedure of stage i) of Example 1 starting from 150 mg of compound obtained in stage c). w=170 mg m/z: ES− 591.5

EXAMPLE 17 a) Octadecylamine 2 g of oleylamine in 120 ml of ethanol are hydrogenated at 30° C. under 8 bar of hydrogen in the presence of palladium-on-charcoal. After reacting for 4 h and evaporating the solvent, 1.6 g of product are obtained in the form of a white powder.

m/z: ES+ 270.7 b) 2-(3,9-Bis(carboxymethyl)-3,6,9,15-tetraazabicyclo[9.3.1]pentadeca-1(14),11(15),12-trien-6-yl)-N-octadecylsuccinamic acid

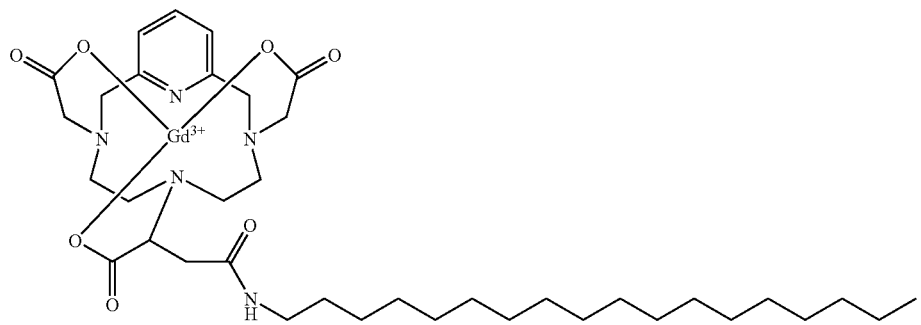

50 mg of the amine prepared in stage a), 70 mg of DCC (dicyclohexylcarbodiimide) and 50 μl of triethylamine are added to a solution of 100 mg of the compound prepared in stage d) of Example 16 in 10 ml of DMF. The medium is stirred at ambient temperature for 18 h and then precipitated from ethanol. The precipitate is filtered off, rinsed with ethyl ether and dried under reduced pressure. After purifying on silica gel, w=70 mg of product are obtained.

m/z: ES− 843

EXAMPLE 18 a) Gadolinium complex of 2-(3,9-bis(carboxymethyl)-3,6,9,15-tetraazabicyclo[9.3.1]pentadeca-1(14),11(15),12-trien-6-yl)-5-(2-octadecylamino-3,4-dioxocyclobut-1-enylamino)pentanoic acid

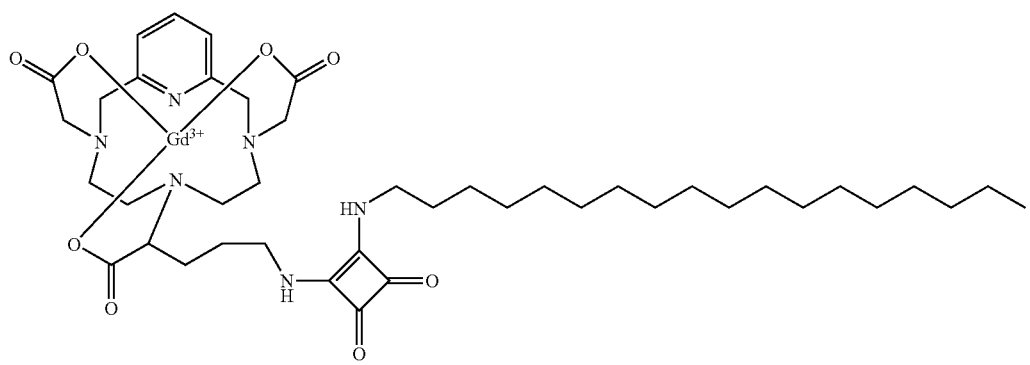

150 mg of the amine prepared in stage a) of Example 17 and 400 mg of the compound prepared in stage a) of Example 14 are suspended in 4 ml of DMSO and three equivalents of triethylamine are added. The mixture is stirred at 50° C. for 24 h. The reaction medium is precipitated from 40 ml of ethanol and the solid obtained is washed with ethyl ether and dried under reduced pressure. w=460 mg m/z: ES+ 940

EXAMPLE 19 b) Gadolinium complex of the 3-[(2-{3,4-dioxo-2-[3-(3,6,9-tris(carboxymethyl)-3,6,9,15-tetraazabicyclo[9.3.1]pentadeca-1(14),11(15),12-trien-13-yl)-propylamino]cyclobut-1-enylamino}ethoxy)hydroxyphosphoryloxy]-2-(octadecanoyloxy)propyl ester of octadecanoic acid

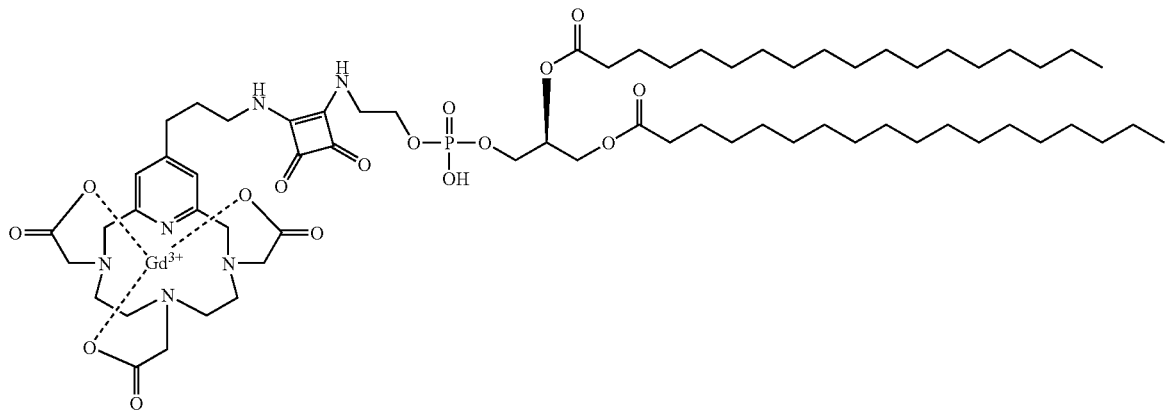

According to the procedure of stage a) of Example 18, starting from 500 mg of the compound prepared in stage a) of Example 12 and 520 mg of DSPE. w=350 mg m/z: ES– 1417

EXAMPLE 20 a) Gadolinium complex of 2-(3,9-bis(carboxymethyl)-3,6,9,15-tetraazabicyclo[9.3.1]pentadeca-1(14),11(15),12-trien-6-yl)-5-hexadecanoylaminopentanoic acid

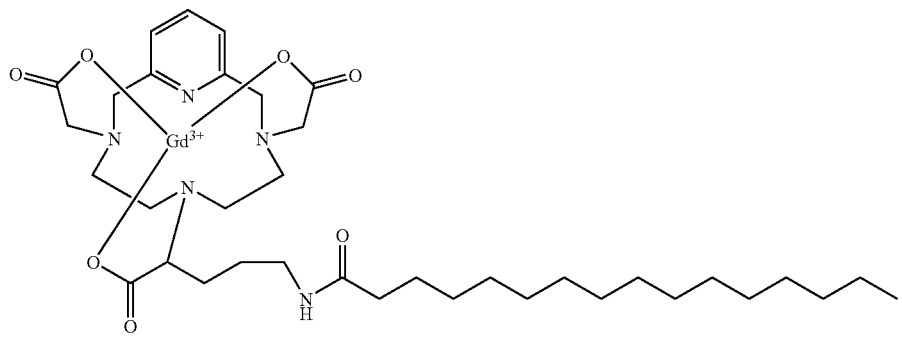

According to the procedure of stage a) of Example 6, starting from the compound obtained in stage c) of Example 13 (300 mg) and 150 mg of palmitoyl chloride. w=230 mg m/z: ES– 829

EXAMPLE 21 a) Gadolinium complex of the 3-({2-[5-(3,9-bis(carboxymethyl)-3,6,9,15-tetraazabicyclo[9.3.1]pentadeca-1(14),11(15),12-trien-6-yl)-5-carboxy-pentanoylamino]ethoxy}hydroxyphosphoryloxy)-2-(hexadecanoyloxy)propyl ester of hexadecanoic acid

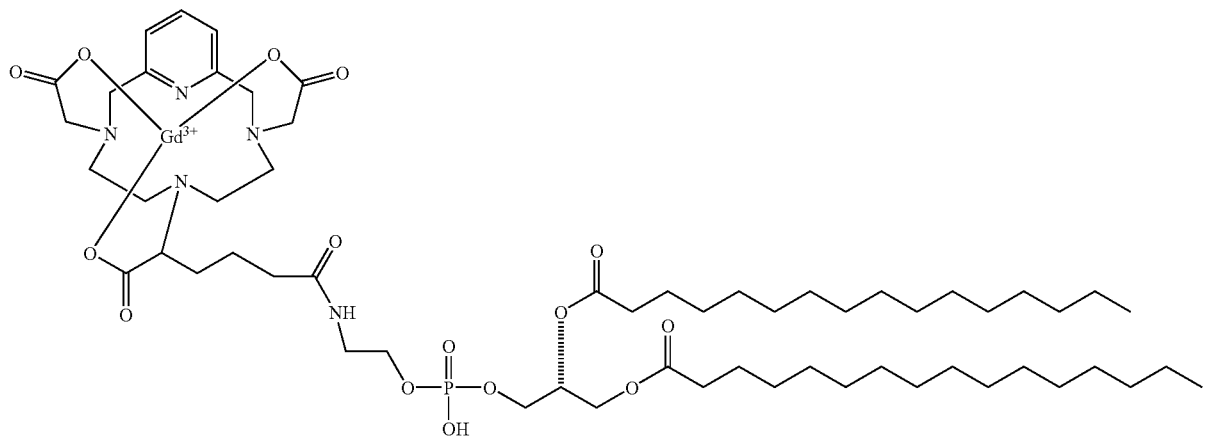

According to the procedure of stage a) of Example 8, starting from 100 mg of the compound prepared in stage d) of Example 15 and 120 mg of DPPE. w=80 mg m/z: ES– 1293

EXAMPLE 22 a) [6,9-Bis(carboxymethyl)-13-(3-(hexadecanoy-lamino)propyl)-3,6,9,15-tetraazabicyclo[9.3.1]penta-deca-1(14),11(15),12-trien-3-yl]acetic acid

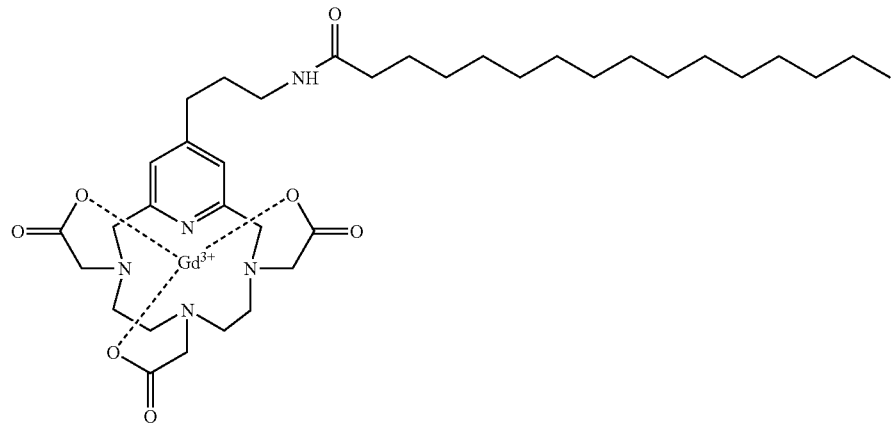

According to the procedure of stage a) of Example 6, starting from the compound obtained in stage f) of Example 11 (150 mg) and 100 mg of palmitoyl chloride. w=110 mg m/z: ES− 829.

The invention claimed is:
1. Compound of formula (I)

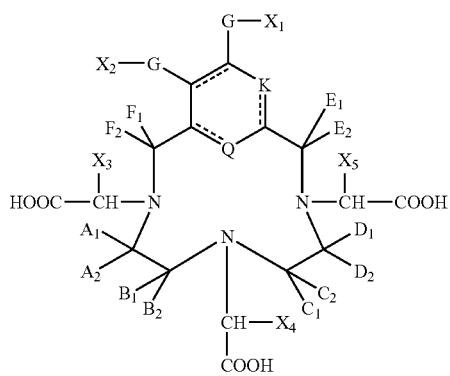

in which:
1) ═══ represents a single or double bond;
2) Q represents a nitrogen atom or an NH radical;
3) $X_1$, $X_2$, $X_3$, $X_4$ and $X_5$, which are identical or different, independently represent, provided that $X_1$, $X_2$, $X_3$, $X_4$ and $X_5$ are not all H and that at least one of $X_1$, $X_2$, $X_3$, $X_4$ and $X_5$ is a liphophilic group:
3.1) a hydrogen atom;
3.2) a $-(CH_2)_a-CONR_1R_2$, $-(CH_2)_a-NR_1COR_2$ or

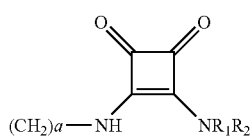

group, with;

a representing 1, 2 or 3;

each $R_1$ or $R_2$ group independently representing an H atom; a substituted or unsubstituted and linear, branched or cyclic $C_7$-$C_{30}$ alkyl or alkenyl chain optionally interrupted by O, NH, $NR_3$ or S, where $R_3$ is a $C_1$-$C_3$ alkyl; or a group

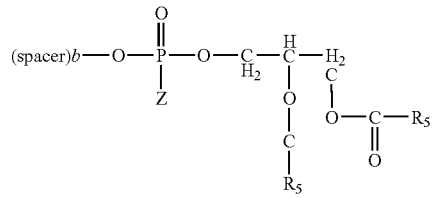

with b representing 0, 1 or 2, Z representing $O^-$ or OH, $R_5$ representing a saturated or unsaturated and optionally substituted group of at least 6 carbon atoms, and spacer representing a $CH_2CH_2$ or polyalkylene glycol group;
3.3) a group

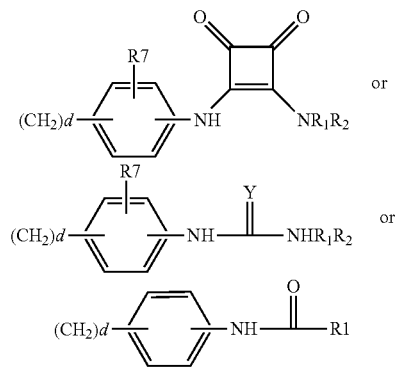

with:
d between 0 and 3;
Y chosen from O and S;
$R_7$ chosen from H, OH, $CH_3$ or $OCH_3$;
$R_1$ and $R_2$ are as defined above;

4) $A_1$, $A_2$, $B_1$, $B_2$, $C_1$, $C_2$, $D_1$, $D_2$, $E_1$, $E_2$, $F_1$ and $F_2$ represent, independently of one another, an H or $CH_3$ or cyclohexyl group;

5) K represents C or N or CH or NH or $N^+R_4$ with $R_4$ being a $C_1$-$C_6$ group chosen from alkyl, benzyl or substituted benzyl;

6) G is not present or represents O or $NHR_4$, with $R_4$ as defined above;

and its pharmaceutically acceptable salts.

2. Compound of formula (I)

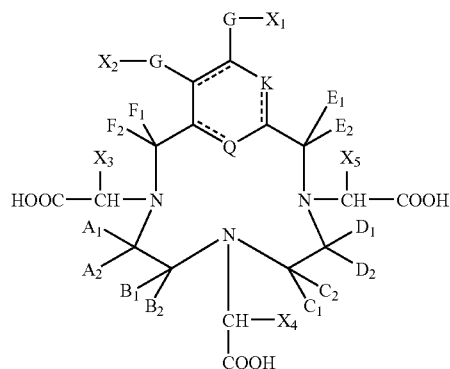
(II)

in which:
1) ⸺represents a single or double bond
2) Q represents a nitrogen atom or an NH radical;
3) $X_1$ or $X_2$, which are identical or different, independently represent a hydrogen atom, a —$(CH_2)_a$—$CONR_1R_2$, —$(CH_2)_a$—$NR_1$—$COR_2$ or

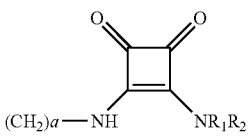

group, with:
a representing 1, 2 or 3;
each $R_1$ or $R_2$ group independently representing an H atom, a substituted or unsubstituted and linear, branched or cyclic $C_7$-$C_{30}$ alkyl or alkenyl chain, or a group

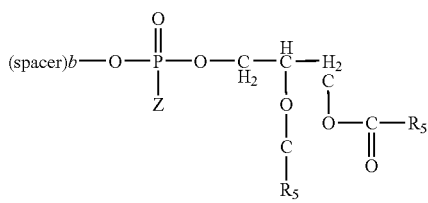

with b representing 0, 1 or 2, Z representing $O^-$ or OH, $R_5$ representing a saturated or unsaturated and optionally substituted group of at least 6 carbon atoms, and spacer representing a $CH_2CH_2$ or polyalkylene glycol group;

4) $X_3$, $X_4$ and $X_5$, which are identical or different, have the same meaning as $X_1$ or $X_2$ provided that $X_1$, $X_2$, $X_3$, $X_4$ and $X_5$ are not all H and at least one of $X_1$, $X_2$, $X_3$, $X_4$ and $X_5$ is a lipophilic group or $X_3$, $X_4$ and $X_5$, which are identical or different, represent

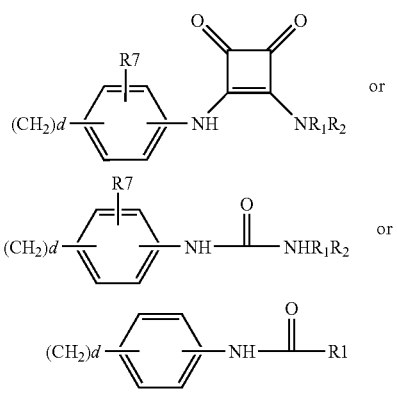

with:
d between 0 and 3;
Y chosen from O and S;
$R_7$ chosen from H, OH, $CH_3$ or $OCH_3$;
$R_1$ and $R_2$ are as defined above;

5) $A_1$, $A_2$, $B_1$, $B_2$, $C_1$, $C_2$, $D_1$, $D_2$, $E_1$, $E_2$, $F_1$ and $F_2$ represent, independently of one another, an H or $CH_3$ or cyclohexyl group;

6) K represents C or N or CH or NH or $N^+R_4$ with $R_4$ a $C_1$-$C_6$ group chosen from alkyl, benzyl or substituted benzyl;

7) G is not present or represents O or $NHR_4$, with $R_4$ as defined above;

and its pharmaceutically acceptable salts.

3. Complex of a paramagnetic metal ion and of an organic chelate of formula (I) according to claim 1.

4. Complex according to claim 3, in which the metal ion is a lanthanide of atomic number 58-70 or a transition metal of atomic number 21-29, 42 or 44.

5. Complex according to claim 3, in which the metal ion is chosen from Gd(III), Mn(II), iron or dysprosium.

6. Physiologically acceptable lipid composition intended for MRI imaging comprising at least one complex according to claim 3.

7. Composition according to claim 6, in the form of an emulsion, of liposomes or of micelles.

8. Composition according to claim 6, comprising water, a dispersed lipid phase, optionally a fluorocarbon and at least one complex according to claim 3.

9. Process for the preparation of a composition according to claim 6, comprising:
    the preparation of a mixture comprising a complex according to claim 3 and an aqueous phase;
    the stirring of the mixture so as to obtain a homogeneous dispersion of the constituents.

10. Compound according to claim 1 or 2, in which $R_1$ and/or $R_2$ represent a $C_7$-$C_{24}$, alkyl or alkenyl chain.

11. Compound of formula (II)

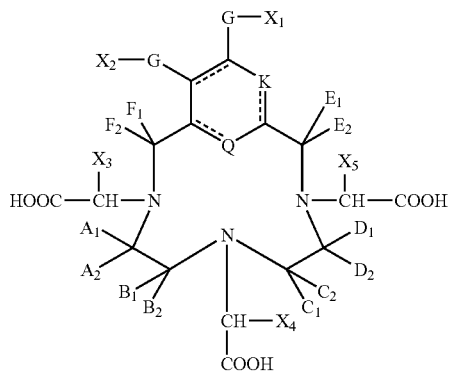

in which:
1) ⚌ represents a single or double bond;
2) $A_1$, $A_2$, $B_1$, $B_2$, $C_1$, $C_2$, $D_1$, $D_2$, $E_1$, $E_2$, $F_1$, $F_2$, Q, K and $R_7$ have the same meaning as in claim 1 or 10, G is not present and $X_1$, $X_2$, $X_3$, $X_4$ or $X_5$, which are identical or different, independently represent $(CH_2)_a$—$NH_2$ or $(CH_2)_a$—$NO_2$ or

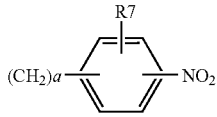

with a representing 1, 2 or 3, or $A_1$, $A_2$, $B_1$, $B_2$, $C_1$, $C_2$, $D_1$, $D_2$, $E_1$, $E_2$, $F_1$, $F_2$, Q, K and $R_7$ have the same meaning as in claim 1 or 10, G represents O or $NHR_4$, in which $R_4$ has the same meaning as in claim 1 or 10, and $X_1$, $X_2$, $X_3$, $X_4$ or $X_5$, which are identical or different, independently represent $(CH_2)_a$—$CO_2H$ or

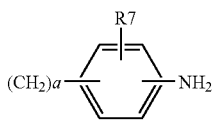

or $(CH_2)_a$—$NH_2$ or $(CH_2)_a$—$NO$, or

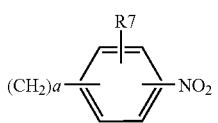

with a representing 1, 2 or 3.

* * * * *

UNITED STATES PATENT AND TRADEMARK OFFICE
CERTIFICATE OF CORRECTION

PATENT NO. : 8,268,810 B2
APPLICATION NO. : 11/886911
DATED : September 18, 2012
INVENTOR(S) : Marc Port It is certified that error appears in the above-identified patent and that said Letters Patent is hereby corrected as shown below:

IN THE SPECIFICATION:

At columns 45-46, correct the compound in Example 19 to read as follows:

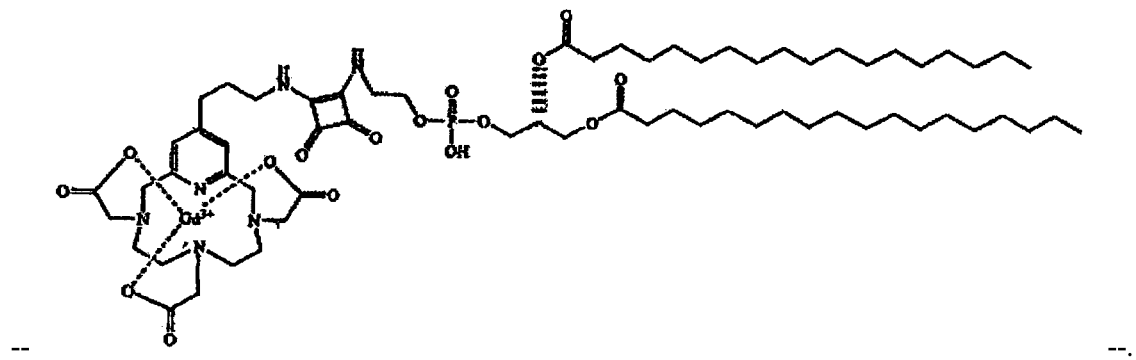

IN THE CLAIMS:

At column 52, in claim 2, correct the second formula, at line 10, to read as follows:

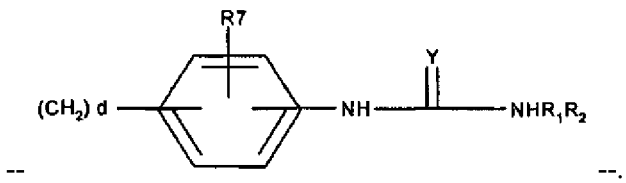

At column 54, in claim 11, line 5, change "as in claim 1 or 10" to --as in claim 1 or 2--.

Signed and Sealed this
Twenty-sixth Day of March, 2013

Teresa Stanek Rea
*Acting Director of the United States Patent and Trademark Office*